(12) United States Patent
Hirata

(10) Patent No.: US 12,038,385 B2
(45) Date of Patent: Jul. 16, 2024

(54) EXAMINATION METHOD, SYSTEM, AND COMPUTER-READABLE MEDIUM

(71) Applicant: EVIDENT CORPORATION, Nagano (JP)

(72) Inventor: Tadashi Hirata, Tokyo (JP)

(73) Assignee: Evident Corporation, Nagano (JP)

( * ) Notice: Subject to any disclaimer, the term of this patent is extended or adjusted under 35 U.S.C. 154(b) by 274 days.

(21) Appl. No.: 17/541,622

(22) Filed: Dec. 3, 2021

(65) Prior Publication Data
US 2022/0091046 A1    Mar. 24, 2022

Related U.S. Application Data

(63) Continuation of application No. PCT/JP2019/026841, filed on Jul. 5, 2019.

(51) Int. Cl.
*G01N 21/80* (2006.01)
*C12M 1/34* (2006.01)

(52) U.S. Cl.
CPC ............. *G01N 21/80* (2013.01); *C12M 41/26* (2013.01); *C12M 41/32* (2013.01); *C12M 41/36* (2013.01)

(58) Field of Classification Search
CPC ....... G01N 21/80; G01N 33/84; C12M 41/26; C12M 41/32; C12Q 1/02
See application file for complete search history.

(56) References Cited

U.S. PATENT DOCUMENTS

| 2003/0127609 A1* | 7/2003 | El-Hage | G01N 21/6452 250/574 |
| 2005/0051723 A1* | 3/2005 | Neagle | C12M 23/50 250/306 |
| 2013/0255374 A1* | 10/2013 | Oura | G01F 23/292 73/293 |

(Continued)

FOREIGN PATENT DOCUMENTS

| JP | S58-204343 A | 11/1983 |
| JP | S58204343 A * | 11/1983 |

(Continued)

OTHER PUBLICATIONS

International Search Report dated Oct. 1, 2019 received in PCT/JP2019/026841.

*Primary Examiner* — Dominic J Bologna
*Assistant Examiner* — Roberto Fabian, Jr.
(74) *Attorney, Agent, or Firm* — Scully, Scott, Murphy & Presser, P.C.

(57) ABSTRACT

A method for examining a culture solution containing a pH indicator and accommodated in a culture container includes: measuring, as a baseline intensity, an intensity of light that has passed through a solution and the culture container; measuring, as a measurement intensity, an intensity of light that has passed through the culture solution and the culture container; obtaining light source information including first information pertaining to the light source that is provided when measuring the baseline intensity and second information pertaining to the light source that is provided when measuring the measurement intensity; and on the basis of the baseline intensity, the measurement intensity, and the light source information, calculating an absorbance of the pH indicator at at least one wavelength included in emitted light from the light source.

21 Claims, 20 Drawing Sheets

(56) References Cited

U.S. PATENT DOCUMENTS

2018/0291328 A1 10/2018 Sasaki et al.
2020/0318058 A1 10/2020 Mochizuki et al.

FOREIGN PATENT DOCUMENTS

| JP | S62-115297 A | 5/1987 | |
| JP | 2013-202031 A | 10/2013 | |
| WO | 2017-104696 A1 | 6/2017 | |
| WO | 2019-124448 A1 | 6/2019 | |
| WO | WO-2019124448 A1 * | 6/2019 | .............. C12M 1/34 |

* cited by examiner

EXAMINATION METHOD, SYSTEM, AND COMPUTER-READABLE MEDIUM

CROSS REFERENCE TO RELATED APPLICATIONS

This is a Continuation Application of PCT Application No. PCT/JP2019/026841, filed Jul. 5, 2019, which was not published under PCT Article 21(2) in English.

BACKGROUND OF THE INVENTION

Field of the Invention

Disclosures herein are related to an examination method, a system, and a computer-readable medium.

Description of the Related Art

It is known that there is a correlation between cell growth and the pH of a culture solution. Thus, in the fields pertaining to cell culturing, the importance of measurement of the pH of a culture solution has been appreciated. In particular, it is known, for example, that as cell culturing advances, a pH indicates acid due to accumulation of a waste product such as lactic acid excreted by cells. Accordingly, a pH may be measured to detect when the pH indicates acid, so that the need to replace a culture medium can be quantitatively recognized in addition to acquiring color information of a pH indicator contained in a culture solution.

pH measurement methods include an electrical measurement method for measuring a pH by soaking electrodes in a culture solution so as to measure a potential difference, and an optical measurement method for measuring a pH by measuring the absorbance of a pH indicator typically contained in a culture solution.

In comparison with the electrical measurement method, the optical measurement method is advantageous in terms of a low risk of occurrence of contamination caused by a measuring action. The optical measurement method is described in, for example, Japanese Laid-open Patent Publication No. 62-115297 and Japanese Laid-open Patent Publication No. 2013-202031.

SUMMARY OF THE INVENTION

An examination method in accordance with an aspect of the present invention is a method for examining a culture solution containing a pH indicator and accommodated in a culture container. The examination method includes: measuring, as a baseline intensity, an intensity of light that is a portion of emitted light from a light source and has passed through a solution not containing the pH indicator and the culture container; measuring, as a measurement intensity, an intensity of light that is a portion of emitted light from the light source and has passed through the culture solution and the culture container; obtaining light source information including first information pertaining to the light source that is provided when measuring the baseline intensity and second information pertaining to the light source that is provided when measuring the measurement intensity; and on the basis of the baseline intensity, the measurement intensity, and the light source information, calculating an absorbance of the pH indicator for at least one wavelength included in emitted light from the light source, wherein: the measuring the baseline intensity includes measuring, as a first baseline intensity, an intensity of light that has passed through the solution and the culture container and has a first wavelength at which the absorbance of the pH indicator is pH-dependent, and measuring, as a second baseline intensity, an intensity of light that has passed through the solution and the culture container and has a second wavelength at which the absorbance of the pH indicator is not pH-dependent; the measuring the measurement intensity includes measuring, as a first measurement intensity, an intensity of light that has the first wavelength and has passed through the culture solution and the culture container, and measuring, as a second measurement intensity, an intensity of light that has the second wavelength and has passed through the culture solution and the culture container; the obtaining the light source information includes obtaining, as the first information, a ratio that is attained when measuring the baseline intensity between the intensity of the emitted light from the light source that has the first wavelength and the intensity of the emitted light from the light source that has the second wavelength, and obtaining, as the second information, a ratio that is attained when measuring the measurement intensity between the intensity of the emitted light from the light source that has the first wavelength and the intensity of the emitted light from the light source that has the second wavelength; and the calculating the absorbance of the pH indicator includes calculating the absorbance of the pH indicator for the first wavelength on the basis of the first baseline intensity, the second baseline intensity, the first measurement intensity, the second measurement intensity, the first information, and the second information.

A system in accordance with an aspect of the present invention includes an image capturing apparatus that has a culture container placed thereon and captures an image of a sample cultured within the culture container, and a control apparatus that controls the image capturing apparatus. The image capturing apparatus includes a light source and a photodetector for detecting emitted light from the light source. The control apparatus measures, as a baseline intensity by using the photodetector, an intensity of light that is a portion of emitted light from the light source and has passed through a solution not containing a pH indicator and the culture container; measures, as a measurement intensity by using the photodetector, an intensity of light that is a portion of emitted light from the light source and has passed through a culture solution containing the pH indicator and the culture container; obtains light source information including first information pertaining to the light source that is provided when measuring the baseline intensity and second information pertaining to the light source that is provided when measuring the measurement intensity; on the basis of the baseline intensity, the measurement intensity, and the light source information, calculates an absorbance of the pH indicator for at least one wavelength included in emitted light from the light source; measures, as a first baseline intensity by using the photodetector, an intensity of light that has passed through the solution and the culture container and has a first wavelength at which the absorbance of the pH indicator is pH-dependent; measures, as a second baseline intensity by using the photodetector, an intensity of light that has passed through the solution and the culture container and has a second wavelength at which the absorbance of the pH indicator is not pH-dependent; measures, as a first measurement intensity by using the photodetector, an intensity of light that has the first wavelength and has passed through the culture solution and the culture container; measures, as a second measurement intensity by using the photodetector, an intensity of light that has the second wavelength and has passed through the culture solution and the culture container; obtains, as the first information, a ratio that is attained when measuring the baseline intensity between the intensity of the emitted light from the light source that has the first wavelength and the intensity of the emitted light from the light source that has the second wavelength; obtains, as the second information, a ratio that is attained when measuring the measurement intensity between the intensity of the emitted light from the light source that has the first wavelength and the intensity of the emitted light from the light source that has the second wavelength; and calculates the absorbance of the pH indicator for the first wavelength on the basis of the first baseline intensity, the second baseline intensity, the first measurement intensity, the second measurement intensity, the first information, and the second information.

A non-transitory computer-readable medium in accordance with an aspect of the present invention has stored therein a program for causing a computer to perform a process including: measuring, as a baseline intensity by using a photodetector, an intensity of light that is a portion of emitted light from a light source and has passed through a solution not containing a pH indicator and a culture container; measuring, as a measurement intensity by using the photodetector, an intensity of light that is a portion of emitted light from the light source and has passed through a culture solution containing the pH indicator and the culture container; obtaining light source information including first information pertaining to the light source that is provided when measuring the baseline intensity and second information pertaining to the light source that is provided when measuring the measurement intensity; on the basis of the baseline intensity, the measurement intensity, and the light source information, calculating an absorbance of the pH indicator for at least one wavelength included in emitted light from the light source; measuring, as a first baseline intensity by using the photodetector, an intensity of light that has passed through the solution and the culture container and has a first wavelength at which the absorbance of the pH indicator is pH-dependent; measuring, as a second baseline intensity by using the photodetector, an intensity of light that has passed through the solution and the culture container and has a second wavelength at which the absorbance of the pH indicator is not pH-dependent; measuring, as a first measurement intensity by using the photodetector, an intensity of light that has the first wavelength and has passed through the culture solution and the culture container; measuring, as a second measurement intensity by using the photodetector, an intensity of light that has the second wavelength and has passed through the culture solution and the culture container; obtaining, as the first information, a ratio that is attained when measuring the baseline intensity between the intensity of the emitted light from the light source that has the first wavelength and the intensity of the emitted light from the light source that has the second wavelength; obtaining, as the second information, a ratio that is attained when measuring the measurement intensity between the intensity of the emitted light from the light source that has the first wavelength and the intensity of the emitted light from the light source that has the second wavelength; and calculating the absorbance of the pH indicator for the first wavelength on the basis of the first baseline intensity, the second baseline intensity, the first measurement intensity, the second measurement intensity, the first information, and the second information.

BRIEF DESCRIPTION OF THE DRAWINGS

The present invention will be more apparent from the following detailed description when the accompanying drawings are referenced.

DESCRIPTION OF THE EMBODIMENTS

In the conventional optical measurement method, it is difficult to stably measure the absorbance of a pH indicator with sufficient accuracy. This is because cell culturing performed for a relatively long period could involve variations in the characteristics of a measurement apparatus during a culture period. In the conventional optical measurement method, variations in the characteristics of a measurement apparatus are not sufficiently considered, and as a result, the measurement accuracy could be reduced during a culture period.

The following describes embodiments of the present invention.

First Embodiment

Figure 1:
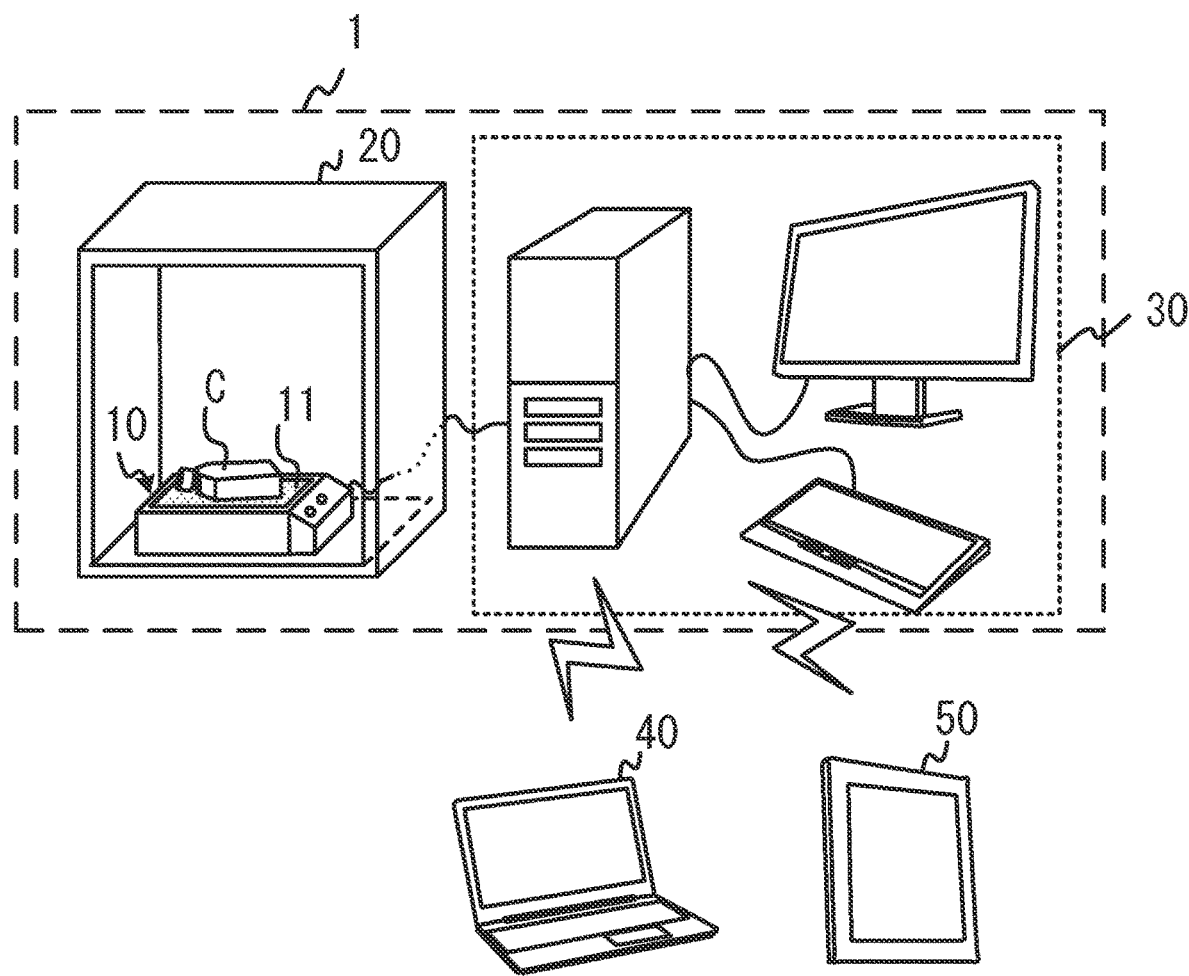
FIG. 1 exemplifies the configuration of a system 1.

FIG. 1 exemplifies the configuration of a system 1. The system 1 depicted in FIG. 1 is a culture monitoring system for monitoring a process of culturing a sample placed within an incubator 20. The system 1 includes an image capturing apparatus 10 that captures an image of a sample cultured within a culture container C, and a control apparatus 30 that controls the image capturing apparatus 10.

The image capturing apparatus 10 is used while placed within the incubator 20, so that the process of culturing the sample can be monitored without the sample being taken out of the incubator 20. More specifically, as depicted in FIG. 1, the image capturing apparatus 10 is placed within the incubator 20 with the culture container C placed on a placement surface 11 thereof. If the culture container C is repeatedly placed in and out of the incubator 20, the cells will be highly likely to be damaged due to a heat shock caused by a temperature change and contamination caused by various germs. Thus, the monitoring of the culturing process is desirably completed without taking the culture container C out of the incubator 20 during culturing.

The control apparatus 30 transmits an image capturing instruction to the image capturing apparatus 10 and receives an image acquired by the image capturing apparatus 10. The control apparatus 30 monitors the growing state of the sample on the basis of an image of the sample acquired by the image capturing apparatus 10.

The control apparatus 30 may display a monitoring result on a display apparatus thereof. The control apparatus 30 may communicate with client terminals (client terminals 40 and 50) and display a monitoring result on the display apparatuses of the client terminals.

FIG. 1 depicts an example in which the image capturing apparatus 10 and the control apparatus 30 are connected by a wired link. However, as long as the image capturing apparatus 10 and the control apparatus 30 can communicate data, the image capturing apparatuses 10 and the control apparatus 30 may be connected wirelessly, rather than by a wired link.

Figure 2:
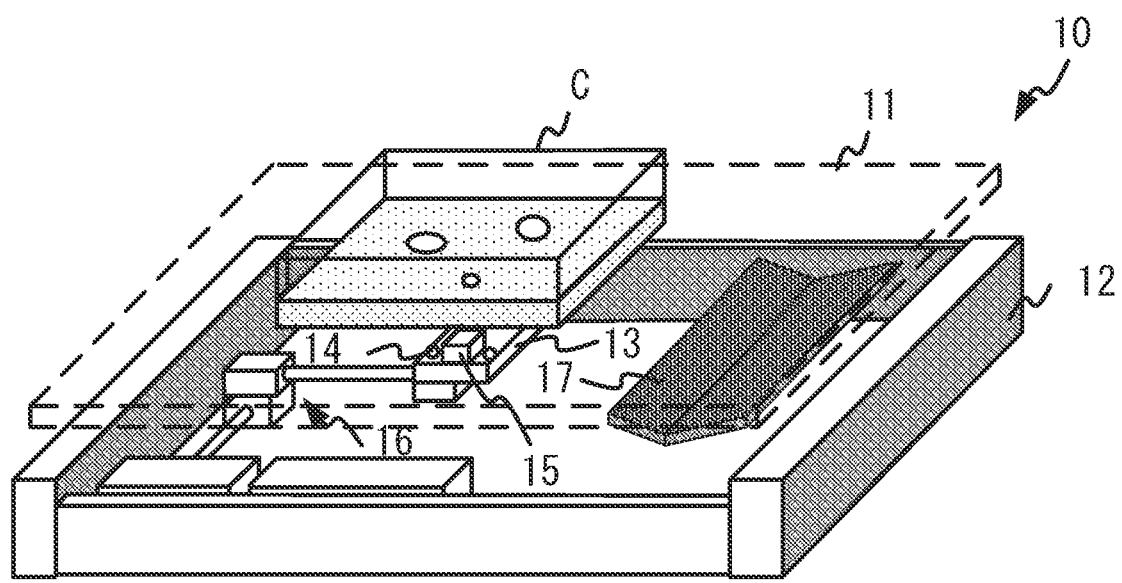
FIG. 2 exemplifies the configuration of an image capturing apparatus 10.
Figure 3:
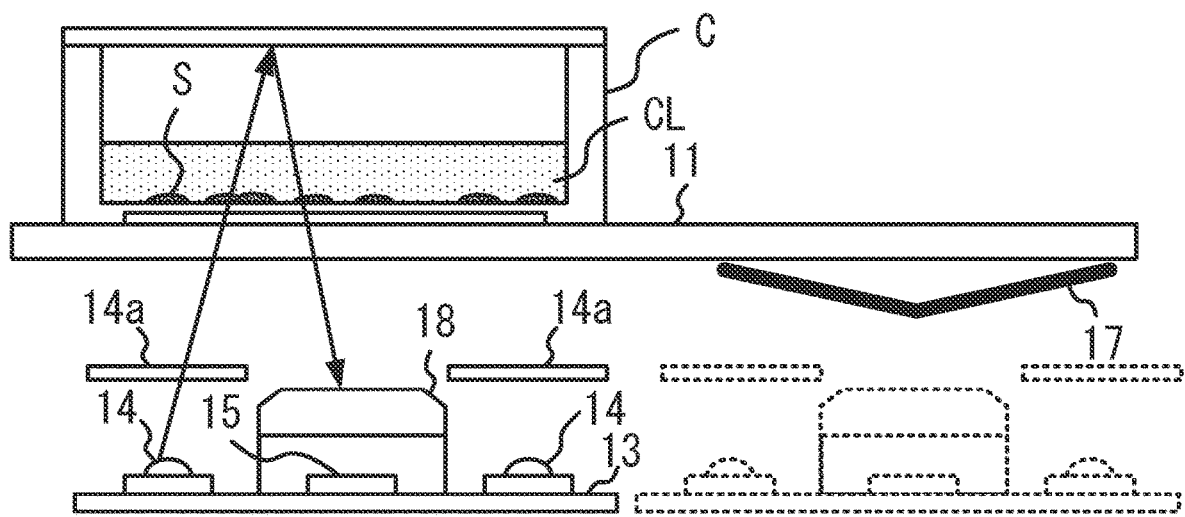
FIG. 3 exemplifies an image capturing apparatus 10 with a stage 13 located at a first measurement position.
Figure 4:
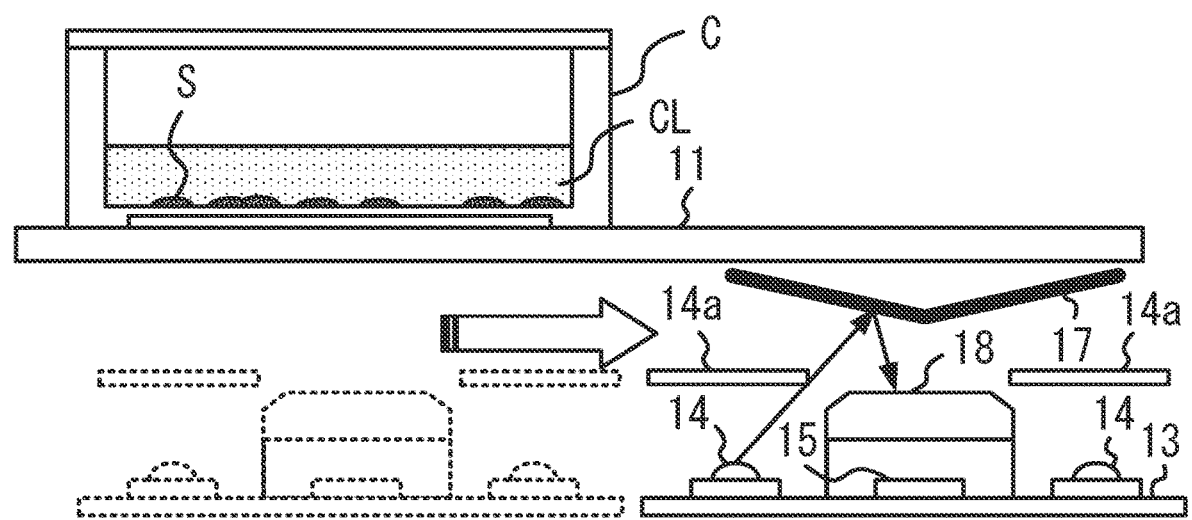
FIG. 4 exemplifies an image capturing apparatus 10 with a stage 13 located at a second measurement position.

FIG. 2 exemplifies the configuration of the image capturing apparatus 10. FIG. 3 exemplifies the image capturing apparatus 10 with a stage 13 located at a first measurement position. FIG. 4 exemplifies the image capturing apparatus 10 with the stage 13 located at a second measurement position. The following describes the image capturing apparatus 10 by referring to FIGS. 2-4.

As depicted in FIG. 2, the image capturing apparatus 10 includes a housing 12. The housing 12 includes a transparent placement surface 11 on which the culture container C is placed. The image capturing apparatus 10 also includes the stage 13, a drive mechanism 16 for moving the stage 13, and a reflection member 17, all of which are positioned within the housing 12 and below the placement surface 11. As depicted in FIGS. 3 and 4, the stage 13 is provided with two light sources 14, an image pickup element 15, and an optical system 18. In particular, in the image capturing apparatus 10, the light sources 14 and the image pickup element 15 are provided within the housing 12, and the light sources 14 move together with the image pickup element 15 in accordance with movement of the stage 13.

The image pickup element 15 is an example of a photodetector that detects emitted light from a light source 14. For example, the image pickup element 15 may be a charge-coupled-device (CCD) image sensor, or a complementary-MOS (CMOS) image sensor. The two light sources 14 may each include, for example, a light emitting diode (LED). The two light sources 14 may be placed opposite to each other with the image pickup element 15 therebetween, or may be placed on only one side of the image pickup element 15. For example, the two light sources 14 may each selectively emit light having a wavelength corresponding to red (R), green (G), or blue (B) by switching between the wavelengths corresponding to the three colors of red (R), green (G), and blue (B).

For example, the drive mechanism 16 may include a drive source such as a motor and move the stage 13 in a direction orthogonal to the optical axis of the optical system 18 (in an XY direction). The drive mechanism 16 moves the stage 13 in the XY direction, thereby allowing the image capturing apparatus 10 to capture images of different regions. The drive mechanism 16 may also move the stage 13 in the direction of the optical axis of the optical system 18 (Z direction). The image capturing apparatus 10 may adjust a focus position by moving the stage 13 in the Z direction by using the drive mechanism 16. Alternatively, the image capturing apparatus 10 may adjust the focus position by moving at least one lens among lenses included in the optical system 18 in the direction of the optical axis.

For example, the reflection member 17 may be a mirror. When the stage 13 is located at a particular position, the reflection member 17 reflects emitted light from a light source 14 toward the image pickup element 15.

As depicted in FIG. 3, when the stage 13 is positioned below the culture container C, light emitted from a light source 14 is incident on an upper surface of the culture container C after traveling via the placement surface 11, the culture container C, and a culture solution CL, and is reflected by the upper surface of the culture container C. In addition, the light reflected by the upper surface of the culture container C is incident on the image pickup element 15 after traveling via the culture solution CL, the culture container C, and the optical system 18. Thus, the image capturing apparatus 10 can measure the intensity of the light that has been weakened by passing through the culture solution CL and the like after being emitted from the light source 14. Meanwhile, by making an adjustment such that the focus position is on the sample S, the image capturing apparatus 10 can acquire an image of the sample S by using the image pickup element 15.

In the meantime, as depicted in FIG. 4, when the stage 13 is positioned below the reflection member 17, emitted light from the light source 14 is reflected by the reflection member 17 without being incident on the placement surface 11 and is incident on the image pickup element 15 after traveling via the optical system 18. In this case, the light emitted from the light source 14 is incident on the image capturing apparatus 10 almost without being weakened. Thus, the image capturing apparatus 10 can measure the intensity of light almost at a time point at which the light is emitted from the light source 14.

Although FIGS. 2-4 illustrate that the mirror is fixed, the mirror may move together with the stage 13, and the angle and position of the mirror may be variable. With such a configuration, simply changing at least either the angle or position of the mirror with the stage 13 positioned below the culture container allows the measuring of light emitted from the light source and reflected by the culture container C and the measuring of light emitted from the light source and reflected by the mirror to be easily switched between.

Figure 5:
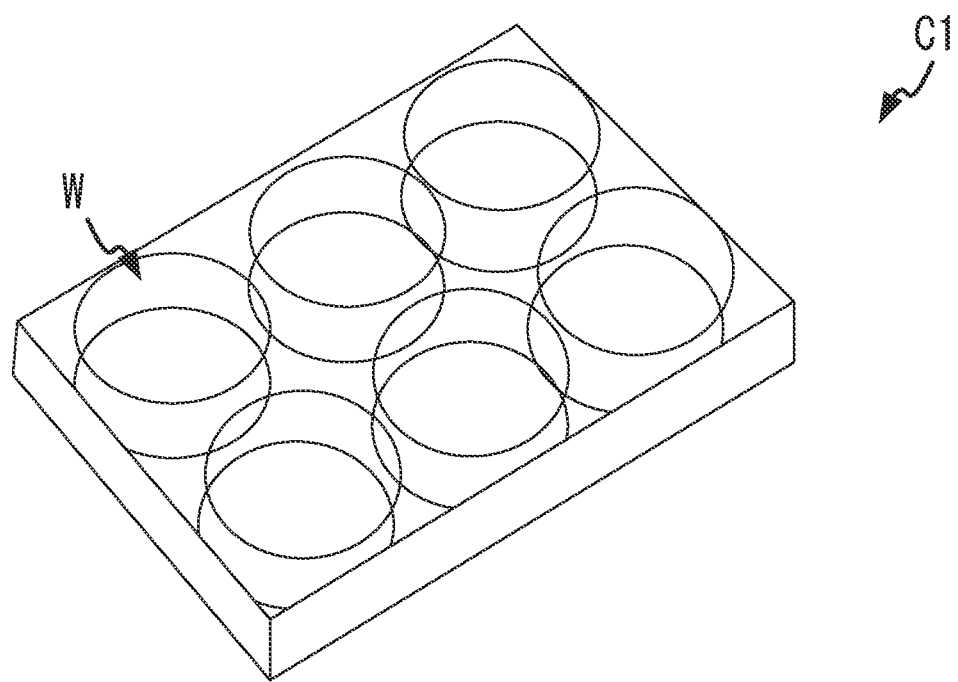
FIG. 5 exemplifies a culture container C1.

FIGS. 1-4 indicate an example in which the culture container C is a flask. However, the culture container C is not limited to a flask. The culture container C may be another culture container, e.g., a culture container C1 depicted in FIG. 5. The culture container C1 is a microwell plate including six wells W.

Figure 6:
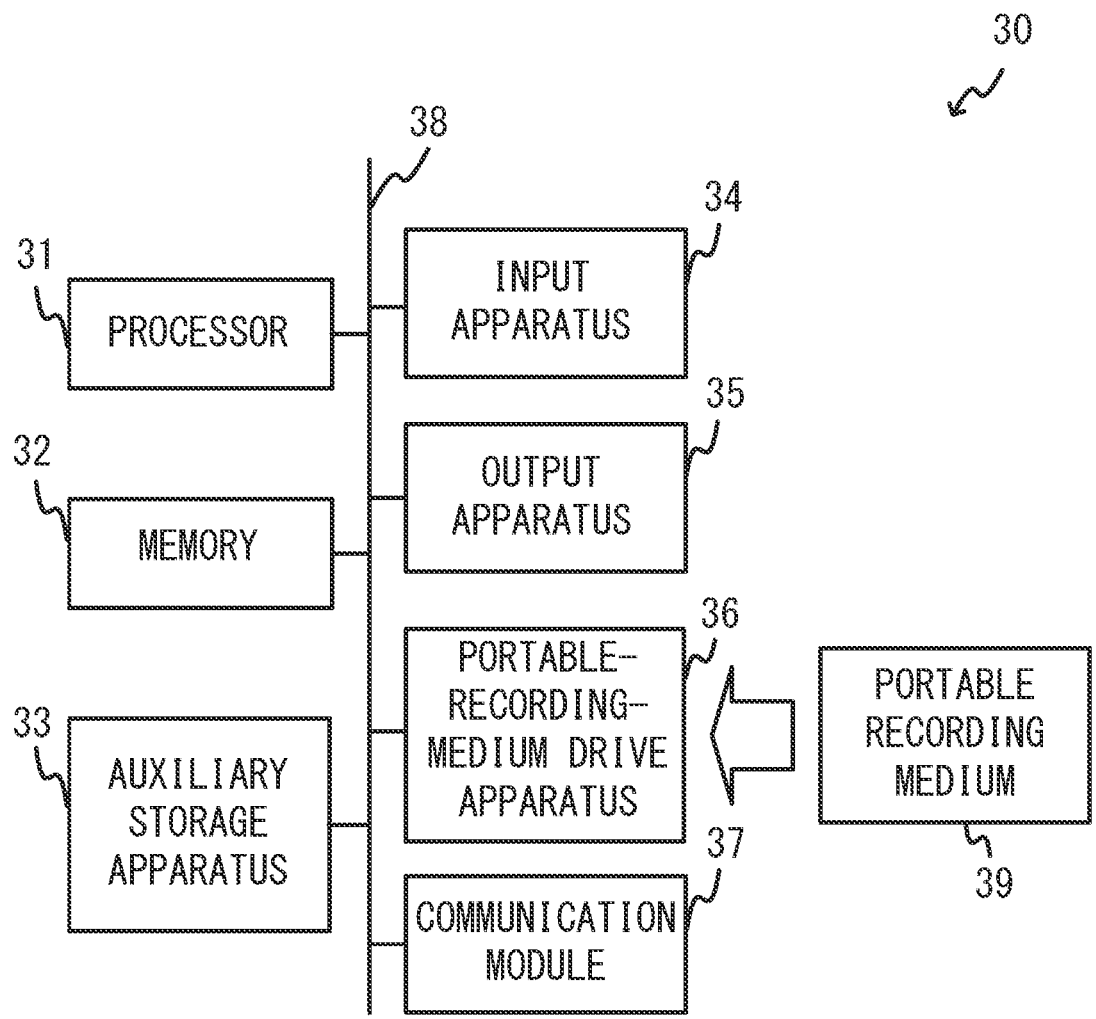
FIG. 6 exemplifies the configuration of a control apparatus 30.

FIG. 6 exemplifies the configuration of a control apparatus 30. The following describes the control apparatus 30 by referring to FIG. 6.

The control apparatus 30 is a computer that controls the system 1. As depicted in FIG. 6, the control apparatus 30 includes a processor 31, a memory 32, an auxiliary storage apparatus 33, an input apparatus 34, an output apparatus 35, a portable-recoding-medium drive apparatus 36 for driving a portable recording medium 39, a communication module 37, and a bus 38. The auxiliary storage apparatus 33 and the portable recording medium 39 are each an example of a non-transitory computer-readable recording medium storing a program.

For example, the processor 31 may be one or more processing circuits of any type that include a central processing unit (CPU) and a graphics processing unit (GPU). The processor 31 performs programmed processing by loading a program stored in the auxiliary storage apparatus 33 or the portable recording medium 39 into the memory 32 and then executing the loaded program.

For example, the memory 32 may be any semiconductor memory such as a random access memory (RAM). In program execution, the memory 32 functions as a work memory for storing a program or data stored in the auxiliary storage apparatus 33 or the portable recording medium 39. For example, the auxiliary storage apparatus 33 may be a nonvolatile memory such as a hard disk or a flash memory. The auxiliary storage apparatus 33 is used mainly to store various data and programs.

The portable-recording-medium drive apparatus 36 accommodates the portable recording medium 39, e.g., an optical disc or Compact Flash®. The portable-recording-medium drive apparatus 36 can output data stored in the memory 32 or the auxiliary storage apparatus 33 to the portable recording medium 39 and read a program, data, and the like from the portable recording medium 39. The portable recording medium 39 may be any recording medium that can be carried. For example, the portable recording medium 39 may include an SD card, a universal serial bus (USB) flash memory, a compact disc (CD), and a digital versatile disc (DVD).

The input apparatus 34 is, for example, a keyboard or a mouse. The output apparatus 35 is, for example, a display apparatus or a printer. For example, the communication module 37 may be a wire communication module that communicates with the image capturing apparatus 10, which is connected via an external port. The communication apparatus 37 may be a wireless communication module. The standard for wireless communication is not particularly limited and may be, for example, Bluetooth®, Low Energy (hereinafter, "BLE"), or Wi-Fi®. The bus 38 connects the processor 31, the memory 32, the auxiliary storage apparatus 33, and the like to each other in a manner such that data can be communicated therebetween.

The configuration depicted in FIG. 6 is an example of the hardware configuration of the control apparatus 30. The control apparatus 30 is not limited to this configuration. The control apparatus 30 may be a general-purpose or special-purpose apparatus. For example, the control apparatus 30 may include a specifically designed electric circuit, e.g., an application specific integrated circuit (ASIC). The control apparatus 30 may be configured using a field-programmable gate array (FPGA).

The control apparatus 30 transmits an image capturing instruction to the image capturing apparatus 10 and then receives an image acquired by the image capturing apparatus 10. The control apparatus 30 calculates, for example, the number and density of cells on the basis of the image acquired by the image capturing apparatus 10, so as to monitor the growing state of the sample S.

In addition to monitoring the growing state of the sample S during a culture period, the system 1 configured as described above can monitor the pH of the culture solution during the period of culturing the sample S by using an optical measurement method using an absorbance. In particular, the system 1 can monitor the pH of the culture solution in consideration of variations in the characteristics of the apparatus that occur during the culture period. The following describes a method implemented by the system 1 for examining a culture solution containing a pH indicator and accommodated within the culture container C1.

First, descriptions are given of a pH measurement method that can be used when variations in the characteristics of the apparatus are not considered, so as to promote an understanding of the pH measurement method implemented by the system 1 in which variations in the characteristics of the apparatus are considered. Unless otherwise noted, the pH measurement methods hereinafter refer to methods for measuring a pH by using the optical measurement method.

In a pH measurement method, the pH of a culture solution is measured by means of the feature wherein a pH indicator exhibits a strongly pH-dependent absorbance at a particular wavelength. In typical cell culturing, a pH indicator added to a culture solution is, in most cases, phenol red (hereinafter, "PR"). The following descriptions are given by taking examples in which the pH indicator is PR.

When the pH indicator is PR, the absorbance of the pH indicator is strongly pH-dependent at a blue (B) wavelength and a green (G) wavelength. Thus, the pH of the culture solution can be measured using the absorbance of PR at the wavelength B and the absorbance of PR at the wavelength G.

More specifically, according to the Lambert Beer Law, an absorbance A is expressed by the product of an absorbance coefficient ε specific to a material, i.e., a constant indicating the extent to which the material absorbs light, an optical path length l in a solution containing a pH indicator (in this case, the optical path length in a culture solution), and a concentration c of the pH indicator in the culture solution.

$$A = \varepsilon c l$$

Only the absorbance coefficient, among the values, is pH-dependent, and even when the pH is constant, the absorbance varies when the optical path length or the concentration varies. Hence, the pH can be calculated from the absorbance of PR under the condition in which the optical path length and the concentration are known. However, the optical path length and the concentration are not necessarily known at the time point at which the pH is measured. Thus, the pH of the culture solution is desirably measured using the ratio between the absorbance of PR at the wavelength B and the absorbance of PR at the wavelength G. This is because the absorbance ratio is substantially equivalent to the absorbance coefficient ratio as a result of the concentration c and the optical path length l being canceled, and the absorbance ratio and the pH have a 1:1 correspondence.

In the pH measurement method, the pH of the culture solution is, as described above, calculated using the ratio between absorbances of the pH indicator. For example, absorbances of the pH indicator may be calculated in accordance with the following formulae when variations in the characteristics of the apparatus are not considered.

$$A_b = -\log_{10}\{(I_b/I_{bw})/(I_r/I_{rw})\} \quad (1)$$

$$A_g = -\log_{10}\{(I_g/I_{gw})/(I_r/I_{rw})\} \quad (2)$$

PR is the pH indicator. $A_b$ is the absorbance of the pH indicator at the wavelength B. $A_g$ is the absorbance of the pH indicator at the wavelength G. $I_b$ is the intensity of light having the wavelength B that is measured with the culture solution CL accommodated in the culture container C1. That is, $I_b$ is the intensity of light having the wavelength B that has passed through the culture solution CL and the culture container C1. Similarly, $I_g$ and $I_r$ are respectively the intensity of light having the wavelength G that has passed through the culture solution CL and the culture container C1 and the intensity of light having the wavelength R that has passed through the culture solution CL and the culture container C1. $I_{bw}$ is the intensity of light having the wavelength B that is measured with water accommodated in the culture container C1. That is, $I_{bw}$ is the intensity of light having the wavelength B that has passed through water and the culture container C1. Similarly, $I_{gw}$ and $I_{rw}$ are respectively the intensity of light having the wavelength G that has passed through water and the culture container C1 and the intensity of light having the wavelength R that has passed through the culture solution CL and the culture container C1. Note that typical culture solutions contain water as a solvent component.

The following describes formulae (1) and (2). The absorbance of a certain material can be expressed by the common logarithm of the ratio between the intensity of light that has passed through the certain object and the intensity of light that has entered the certain object (=(intensity of light that has passed through the certain object)/(intensity of light that has entered the certain object)). Thus, determining the intensity of light that has passed through the pH indicator and the intensity of light that has entered the pH indicator allows for calculation of the absorbance of the pH indicator.

In formulae (1) and (2), the intensity of light that has passed through the pH indicator is defined as the intensity $I_b$ when calculating the absorbance at the wavelength B, and the intensity of light that has passed through the pH indicator is defined as the intensity $I_g$ when calculating the absorbance at the wavelength G. By contrast, the intensity of light that has entered the pH indicator is defined as the intensity $I_r$ when calculating the absorbance at the wavelength B or when calculating the absorbance at the wavelength G. This is because at the red (R) wavelength, the absorbance of PR is not pH-dependent and is almost 0, so it can be considered that there is no absorption. The optical intensity $I_r$ at the wavelength R at which the pH indicator exhibits no absorption can be measured and defined as the intensity obtained when light having the wavelength G or B enters the pH indicator, and can be used in the denominator, so that wavelength-independent noise generated during culturing can be corrected. Specifically, the noise may be, for example, the fogging of the container and a concentration change caused by evaporation of the culture solution. The noise occurs during culturing and thus cannot be corrected in baseline measurement performed before the culturing starts.

More specifically, when measuring the intensities $I_b$, $I_g$, and $I_r$, the light for which the measurement is performed passes through not only the pH indicator but also the other components of the culture solution CL and the culture container C1. To facilitate understanding, it should be assumed that the light passes through the pH indicator after passing through the other components of the culture solution CL and the culture container C1. Under this condition, the intensities $I_b$ and $I_g$ are each the intensity of light that has passed through the pH indicator. The pH indicator does not absorb light having the wavelength R, so it can be said that the intensity $I_r$ is the intensity of light that has passed through the pH indicator and is also the intensity of light that has entered the pH indicator. Accordingly, assuming that the intensities of light rays having the wavelengths R, G, and B that have entered the pH indicator are the same, the absorbance of the pH indicator at the wavelength B can be calculated by the common logarithm of the ratio $(I_b/I_r)$.

Likewise, the absorbance of the pH indicator at the wavelength G can be calculated by the common logarithm of the ratio $(I_g/I_r)$.

However, the intensities of light rays having the wavelengths R, G, and B that have entered the pH indicator are not necessarily the same. Thus, the difference between B, G, and R in intensity of light that has entered the pH indicator is corrected by assuming for formula (1), that $(I_{bin}/I_r)=(I_{bw}/I_{rw})$ is satisfied and by assuming for formula (2), that $(I_{gin}/I_r)=(I_{gw}/I_{rw})$ is satisfied. In this example, $I_{bin}$ is the intensity of light having the wavelength B that has entered the pH indicator. $I_{gin}$ is the intensity of light having the wavelength G that has entered the pH indicator. $I_{bw}$, $I_{gw}$, and $I_{rw}$ are each, as described above, the intensity of light having a wavelength that has passed through water and the culture container C1, and each essentially means the intensity of light having a wavelength that has passed through the components of the culture solution CL excluding the pH indicator, and the culture container C1.

As described above, even when the intensity $I_{bin}$ ($I_{gin}$) of light having the B (G) wavelength that has entered the pH indicator is unknown, the ratio between the intensity of light having the B (G) wavelength that has entered the pH indicator and the intensity of light having the wavelength R that has entered the pH indicator can be estimated using the values of $I_{bw}$ ($I_{gw}$), $I_{rw}$, and $I_r$. For formulae (1) and (2), the differences in intensity between the wavelengths are corrected using such characteristics. Note that the ratio in light intensity between wavelengths is hereinafter referred to as a "wavelength intensity ratio."

In the meantime, when the wavelength intensity ratio between light rays emitted from the light source 14 changes, the wavelength intensity ratio between light rays that enter the pH indicator also changes. However, $I_{bw}$, $I_{gw}$, and $I_{rw}$ are each the intensity of light measured while water is in the culture container C1. That is, $I_{bw}$, $I_{gw}$, and $I_{rw}$ are each the intensity of light measured before the culture solution is poured in the culture container C1, i.e., before the culturing starts. After the culturing of the sample S starts with the culture container C1 containing the culture solution CL, $I_{bw}$, $I_{gw}$, and $I_{rw}$ cannot be remeasured without removing the culture solution CL from the cell culturing. Hence, variations that occur in output from the light source after the culturing starts are not reflected in $I_{bw}$, $I_{gw}$, and $I_{rw}$. With respect to formulae (1) and (2), accordingly, when the wavelength intensity ratio between emitted light rays from the light source 14 changes after the culturing starts, the difference in intensity of light that enters the pH indicator cannot be correctly corrected between B, G, and R.

The following pH measurement method implemented by the system 1 is provided in consideration of the above-described facts. This method allows for correct calculation of the absorbance of a pH indicator even when the characteristics of the apparatus vary, in particular when the wavelength intensity ratio between emitted light rays from the light source 14 changes.

Figure 7:
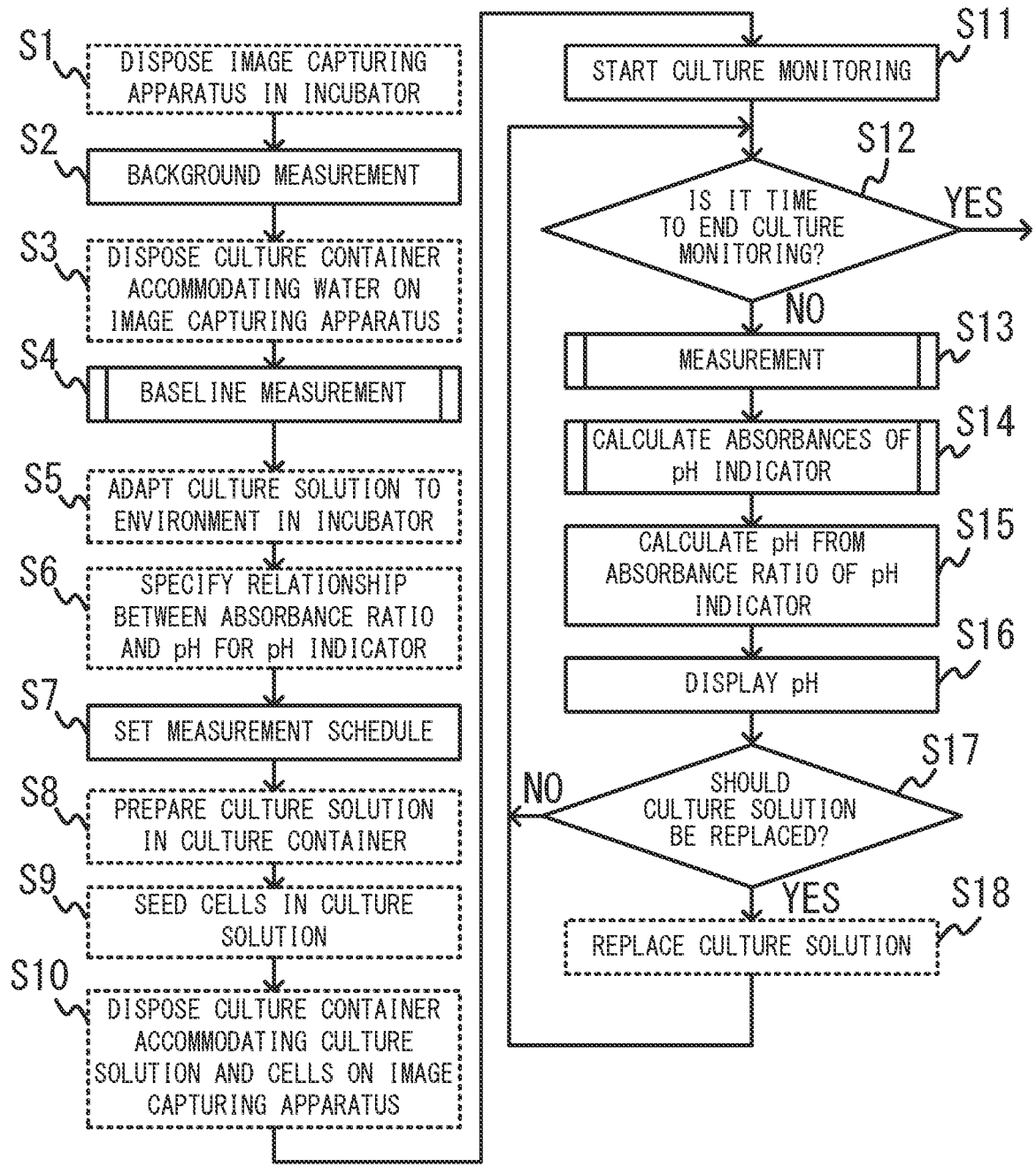
FIG. 7 is a flowchart illustrating an example of a method for monitoring the pH of a culture solution.
Figure 8:
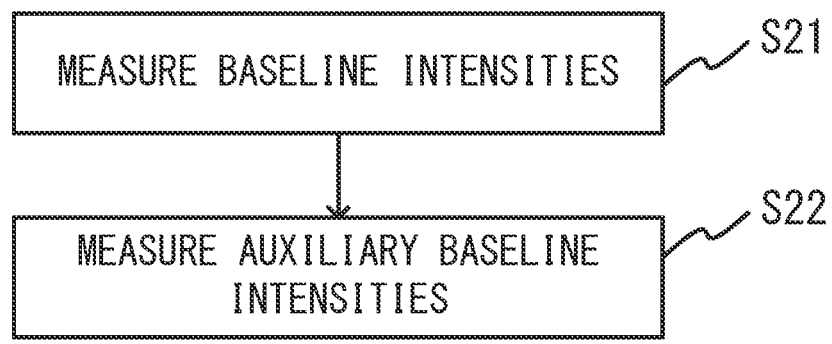
FIG. 8 is a flowchart illustrating details of baseline measurement.
Figure 9:
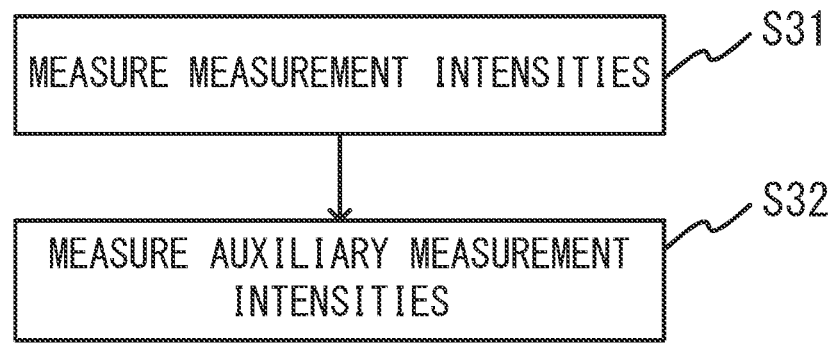
FIG. 9 is a flowchart illustrating details of measurement after culture monitoring.
Figure 10:
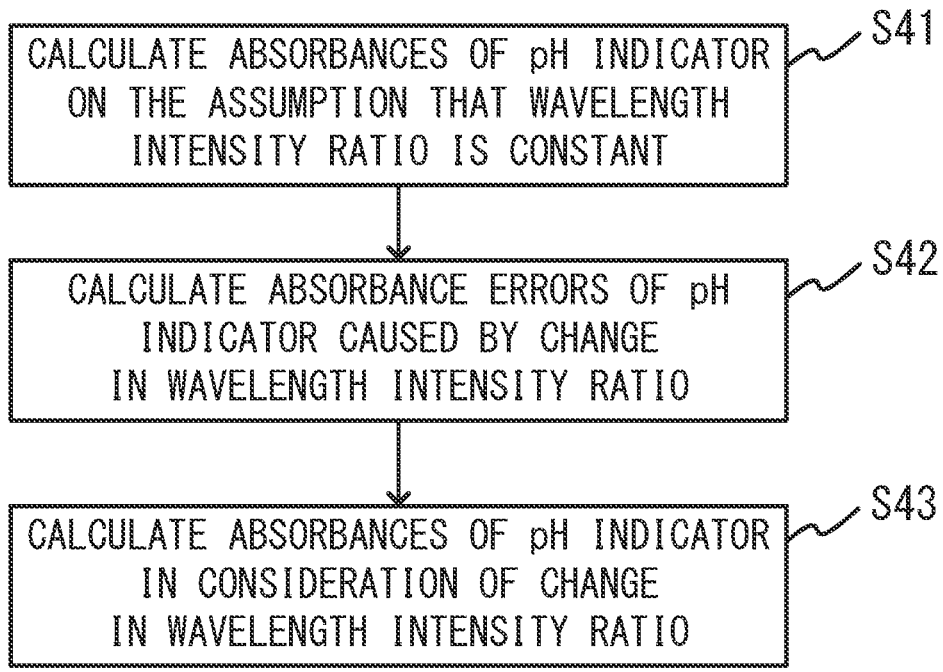
FIG. 10 is a flowchart illustrating details of calculation of an absorbance.
Figure 11:
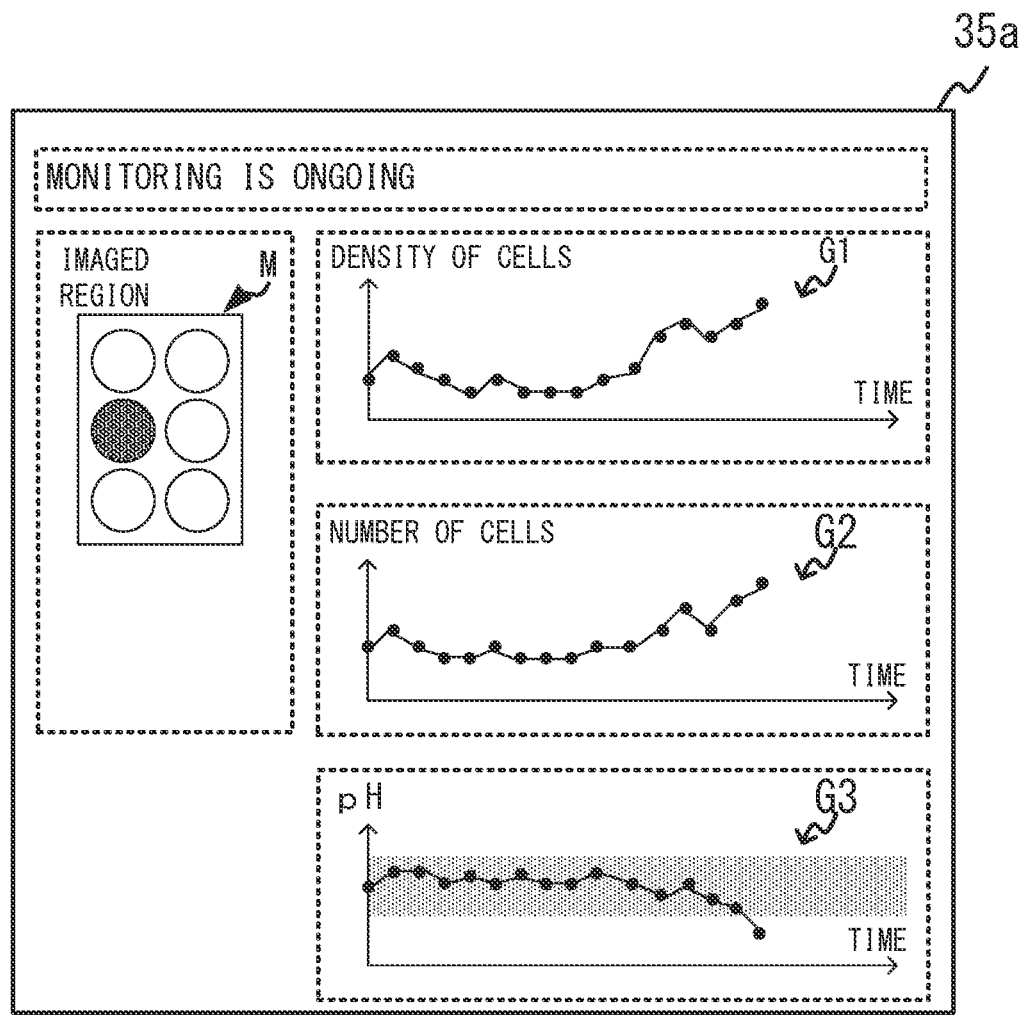
FIG. 11 illustrates an example of a screen displayed during monitoring.

FIG. 7 is a flowchart illustrating an example of a method for monitoring the pH of a culture solution. Note that the solid-line blocks in FIG. 7 indicate processes performed by the system 1, and the dotted-line blocks therein indicate processes performed by the user of the system 1. FIG. 8 is a flowchart illustrating details of baseline measurement. FIG. 9 is a flowchart illustrating details of measurement after culture monitoring. FIG. 10 is a flowchart illustrating details of calculation of an absorbance. FIG. 11 illustrates an example of a screen displayed during monitoring. By referring to FIGS. 7-11, the following describes a method implemented by the system 1 for examining a culture solution, more specifically a method wherein the absorbance of a pH indicator is calculated, and the pH of the culture solution is measured and monitored. The following descriptions are given by taking examples in which the pH indicator is PR.

First, the user disposes the image capturing apparatus 10 in the incubator 20 (step S1). Then, the control apparatus 30 performs background measurement by controlling the image capturing apparatus 10 (step S2). In the background measurement, the control apparatus 30 measures an optical intensity by using the image pickup element 15 without illumination. The optical intensity measured in the background measurement is used to subtract an intensity caused by a dark current from the optical intensity measured by the image pickup element 15 in baseline measurement and in measurement after the start of culturing (both of the measurements are described hereinafter).

When the background measurement is finished, the user disposes a culture container C1 accommodating water on the image capturing apparatus 10 (step S3). Then, the control apparatus 30 performs the baseline measurement indicated in FIG. 8 by controlling the image capturing apparatus 10 (step S4).

In the baseline measurement in step S4, the control apparatus 30 first measures baseline intensities (step S21). In particular, the control apparatus 30 moves the image pickup element 15 to a first position indicated in FIG. 3 by moving the stage 13 to a position below the culture container C1 containing water. The first position is an example of a position on which light that is a portion of emitted light from a light source 14 and has passed through the culture container C1 is incident. Afterward, by controlling the image capturing apparatus 10, the control apparatus 30 measures, as the baseline intensity by using the image pickup element 15, the intensity of light that is a portion of emitted light from the light source 14 and has passed through water and the culture container C1. Note that water is an example of a solution not containing a pH indicator and is a solvent containing the culture solution CL.

The baseline intensity is measured for each of light having the wavelength R, light having the wavelength G, and light having the wavelength B. In particular, the light source 14 emits rays of light having the wavelengths R, G, and B, and the control apparatus 30 measures a baseline intensity $I_{rw}$ of the light having the wavelength R, a baseline intensity $I_{gw}$ of the light having the wavelength G, and a baseline intensity $I_{bw}$ of the light having the wavelength B. Note that the wavelength B, the wavelength R, and the wavelength G are respectively examples of a first wavelength at which the absorbance of the pH indicator is pH-dependent, a second wavelength at which the absorbance of the pH indicator is not pH-dependent, and a third wavelength at which the absorbance of the pH indicator is pH-dependent. The baseline intensities $I_{bw}$, $I_{rw}$, and $I_{gw}$ are respectively examples of first, second, and third baseline intensities.

Furthermore, the control apparatus 30 measures auxiliary baseline intensities (step S22), and ends the baseline measurement indicated in FIG. 8. In particular, the control apparatus 30 moves the image pickup element 15 to a second position indicated in FIG. 4 by moving the stage 13 to a position below the reflection member 17. The second position is an example of a position on which light that is a portion of emitted light from the light source 14 and does not pass through the culture solution CL is incident. Afterward, by controlling the image capturing apparatus 10, the control apparatus 30 measures, as the auxiliary baseline intensity by using the image pickup element 15, the intensity of light incident on the image pickup element 15 located at the second position.

The auxiliary baseline intensity is measured for each of light having the wavelength R, light having the wavelength G, and light having the wavelength B. In particular, the light source 14 emits rays of light having the wavelengths R, G, and B, and the control apparatus 30 measures an auxiliary baseline intensity $I_{rw}'$ of light having the wavelength R, an auxiliary baseline intensity $I_{gw}'$ of light having the wavelength G, and an auxiliary baseline intensity $I_{bw}'$ of light having the wavelength B. The auxiliary baseline intensities $I_{bw}'$, $I_{rw}'$, and $I_{gw}'$ are respectively examples of first, second, and third auxiliary baseline intensities.

Furthermore, in step S22, the control apparatus 30 obtains the ratio between the auxiliary baseline intensities $I_{bw}'$ and $I_{rw}'$ as first information on the basis of the measurement result. The control apparatus 30 also obtains the ratio between the auxiliary baseline intensities $I_{gw}'$ and $I_{rw}'$ as third information on the basis of the measurement result. Note that the first information and the third information can be deemed as an inter-wavelength intensity ratio of the light source 14 that is attained when measuring a baseline intensity and also as information pertaining to the light source 14 that is provided when measuring a baseline intensity.

After the baseline intensities are measured, the culture solution CL is poured in the container, and the container is set within the incubator 20 and adapted to the environment therein for the purpose of avoiding heat shock (step S5). When the inside and the outside of the incubator 20 are different in terms of temperature and $CO_2$ concentration, the pH value cannot be correctly measured if various measurements are performed soon after the culture solution CL is set within the incubator 20. To avoid this, it is desirable that the container containing the culture solution be stationarity placed within the incubator for a certain time period. The container used in the measurement may be the same as or different from the container accommodating the culture solution CL in step S5, but the same container is desirably used to prevent a pH change that could occur if the containers are switched.

The culture solution CL does not necessarily need to be set within the incubator 20 after the baseline measurement is performed. Before the baseline measurement is performed, i.e., at a desirable timing in the processes of steps S1-S3, the culture solution may be disposed within the incubator 20 so as to be adapted to the environment therein.

After the baseline measurement is finished, the user specifies the relationship between an absorbance ratio and a pH for the pH indicator contained in the culture solution CL (step S6). Step S6 can be omitted when the relationship between the absorbance ratio and the pH of the pH indicator is already known.

In step S6, the user prepares a plurality of pH-adjustment culture solutions with different pHs. For example, the pH-adjustment culture solutions may each be obtained by adding an acid substance (e.g., citric acid) or a basic substance to the culture solution CL set within the incubator 20 in step S5. The user measures the pHs of the plurality of pH-adjustment culture solutions by using an electrical measurement method with a pH measuring instrument. Then, the user disposes a culture container C1 accommodating the pH-adjustment culture solution on the image capturing apparatus 10 within the incubator 20. By performing processes similar to those of steps S12 and S13 (described hereinafter), the control apparatus 30 calculates the absorbance of the pH indicator contained in the pH-adjustment culture solution at the wavelength B and that at the wavelength G. In addition, the control apparatus 30 calculates, for each of the pH-adjustment culture solutions, the common logarithm of the ratio between the absorbance at the wavelength B and the absorbance at the wavelength G. Finally, by using the pHs measured for the plurality of pH-adjustment culture solutions and the common logarithms of the absorbance ratios of the pH indicator calculated for the plurality of pH-adjustment culture solutions, the control apparatus 30 specifies the relationship between the absorbance ratio and pH of the pH indicator. In particular, points specified by the pHs and the common logarithms of the absorbance ratios of the pH indicator are plotted and linearly interpolated to calculate the slope and intercepts of a linear function expressing the relationship between the pH and the common logarithm of the absorbance ratio of the pH indicator. When only either of the wavelengths B and G is used, the linear function may have the absorbance at the wavelength B or G as a variable, instead of the absorbance ratio of the pH indicator. In this case, it is assumed that culture conditions such as the amount of culture solution and concentration are known and exhibit no changes during culturing. Especially when PR is used as a pH indicator, the absorbance at the wavelength G is desirably used because the absorbance at the wavelength G exhibits a larger change associated with pH than the absorbance at the wavelength B.

When the culturing is performed for the second time or after, the processes of steps S1-S6 may be omitted under the condition in which the same culture container and the same culture solution are used.

Afterward, the control apparatus 30 sets a measurement schedule in accordance with user input (step S7). In this case, for example, a cycle for the measurement in step S13 (described hereinafter), an end time for culture monitoring, and a monitoring position for the culture solution CL may be set.

When the preparation is finished, the user again prepares the culture solution CL in the culture container C1 (step S8) and seeds cells in the culture solution CL as a sample S (step S9). Finally, the user disposes a culture container C1 accommodating the culture solution CL and the cells on the image capturing apparatus 10 within the incubator 20 (step 310). Then, the control apparatus 30 starts culture monitoring (step S11).

Upon the monitoring being started, the control apparatus 30 repeats the processes of steps S13-S17 until the end time of the culture monitoring (YES in step S12). Although not illustrated in FIG. 7, during the culture monitoring, the system 1 periodically acquires images of the sample 5, and the control apparatus 30 calculates the number and density of the cells, which indicate the growing state of the sample S.

At measurement times, by controlling the image capturing apparatus 10, the control apparatus 30 performs the measurement indicated in FIG. 9 so as to examine the culture solution CL (step S13).

In the measurement in step S13, the control apparatus 30 first measures measurement intensities (step S31). In particular, the control apparatus 30 moves the image pickup element 15 to the first position indicated in FIG. 3 by moving the stage 13 to a position below the culture container C1 containing the culture solution CL. Afterward, by controlling the image capturing apparatus 10, the control apparatus 30 measures, as the measurement intensity by using the image pickup element 15, the intensity of light that is a portion of emitted light from the light source 14 and has passed through the culture solution CL and the culture container C1.

The measurement intensity is measured for each of light having the wavelength R, light having the wavelength G, and light having the wavelength B. In particular, the light source 14 emits rays of light having the wavelengths R, G, and B, and the control apparatus 30 measures a measurement intensity $I_r$ of the light having the wavelength R, a measurement intensity $I_g$ of the light having the wavelength G, and a measurement intensity $I_b$ of the light having the wavelength B. The measurement intensities $I_b$, $I_r$, and $I_g$ are respectively examples of first, second, and third measurement intensities.

Furthermore, the control apparatus 30 measures auxiliary measurement intensities (step S32), and ends the measurement indicated in FIG. 9. In particular, the control apparatus 30 moves the image pickup element 15 to the second position indicated in FIG. 4 by moving the stage 13 to a position below the reflection member 17. Afterward, by controlling the image capturing apparatus 10, the control apparatus 30 measures, as the auxiliary measurement intensity by using the image pickup element 15, the intensity of light incident on the image pickup element 15 located at the second position.

The auxiliary measurement intensity is measured for each of light having the wavelength R, light having the wavelength G, and light having the wavelength B. In particular, the light source 14 emits rays of light having the wavelengths R, G, and B, and the control apparatus 30 measures an auxiliary measurement intensity $I_r'$ of the light having the wavelength R, an auxiliary measurement intensity $I_g'$ of the light having the wavelength G, and an auxiliary measurement intensity $I_b'$ of the light having the wavelength B. The auxiliary measurement intensities $I_b'$, $I_r'$ and $I_g'$ are respectively examples of first, second, and third auxiliary measurement intensities.

Furthermore, in step S32, the control apparatus 30 obtains the ratio between the auxiliary measurement intensities $I_b'$ and $I_r'$ as second information on the basis of the measurement result. The control apparatus 30 also obtains the ratio between the auxiliary measurement intensities $I_g'$ and $I_r'$ as fourth information on the basis of the measurement result. Note that the second information and the fourth information can be deemed as the wavelength intensity ratio of the light source 14 that is attained when measuring a measurement intensity and also as information pertaining to the light source 14 that is provided when measuring a measurement intensity.

When the measurement is finished, the control apparatus 30 calculates absorbances of the pH indicator (step S14). In step S14, the three processes indicated in FIG. 10 are performed.

Specifically, the control apparatus 30 first calculates absorbances of the pH indicator on the assumption that the wavelength intensity ratio between emitted light rays from the light source 14 at the time of the baseline measurement in step S4 and the wavelength intensity ratio between emitted light rays from the light source 14 at the present time are the same (step S41). In step S41, on the basis of the baseline intensities measured in step S21 and the measurement intensities measured in step S31, the control apparatus 30 calculates the absorbance $A_b$ of the pH indicator at the wavelength B and the absorbance $A_g$ of the pH indicator at the wavelength G by using formulae (1) and (2).

Afterward, the control apparatus 30 calculates absorbance errors of the pH indicator that are caused by a change in the wavelength intensity ratio (step S42). In step S42, on the basis of the auxiliary baseline intensities measured in step S22 and the auxiliary measurement intensities measured in step S32, the control apparatus 30 calculates an absorbance error $A_b'$ of the pH indicator at the wavelength B and an absorbance error $A_g'$ of the pH indicator at the wavelength G by using the following formulae (3) and (4).

$$A_b' = -\log_{10}(I_b'/I_{bw}')/(I_r'/I_{rw}') \quad (3)$$

$$A_g' = -\log_{10}(I_g'/I_{gw}')/(I_r'/I_{rw}') \quad (4)$$

The expression $(I_b'/I_{bw}')/(I_r'/I_{rw}')$ in formula (3) can be transformed to $(I_b'/I_r')/(I_{bw}'/I_{rw}')$. The expression $(I_{bw}'/I_{rw}')$ is the first information obtained in step S22 and is the ratio between the intensities of light rays having the wavelength B and the wavelength R emitted from the light source 14 when measuring the baseline intensities. The expression $(I_b'/I_r')$ is the second information obtained in step S32 and is the ratio between the intensities of light rays having the wavelength B and the wavelength R emitted from the light source 14 when measuring the measurement intensities. Thus, the expression $(I_b'/I_{bw}')/(I_r'/I_{rw}')$ in formula (3) indicates a change in the wavelength intensity ratio between the wavelength B and the wavelength R of light rays emitted from the light source 14 that occurs during the period from the baseline measurement in step S4 to the measurement in step S12. Accordingly, the value $A_b'$ in formula (3) is obtained by converting the change in the wavelength intensity ratio between the wavelength B and the wavelength R into an absorbance and indicates an absorbance error caused by the change in the wavelength intensity ratio between the wavelength B and the wavelength R. Likewise, the value $A_g'$ in formula (4) indicates an absorbance error caused by a change in the wavelength intensity ratio between the wavelength G and the wavelength R.

After calculating the absorbance errors, the control apparatus 30 calculates absorbances of the pH indicator in consideration of the changes in the wavelength intensity ratios (step S43). In this case, as indicated by formulae (5) and (6), the control apparatus 30 subtracts the absorbance errors calculated in step S42 from the absorbances calculated in step S41 so as to calculate an absorbance $A_B$ of the pH indicator at the wavelength B and an absorbance $A_G$ of the pH indicator at the wavelength G in consideration of the changes in the wavelength intensity ratios.

$$A_B = A_b - A_b' \quad (5)$$

$$A_G = A_g - A_g' \quad (6)$$

As described above, in step S14, the control apparatus 30 calculates absorbances of the pH indicator on the basis of the baseline intensities measured in step S21, the measurement intensities measured in step S31, and the light source information obtained in steps S22 and S32. More specifically, the control apparatus 30 calculates the absorbance of the pH indicator at the first wavelength (B) on the basis of the first baseline intensity (B), the second baseline intensity (R), the first measurement intensity (B), the second measurement intensity (R), the first information, and the second information. The control apparatus 30 calculates the absorbance of the pH indicator at the third wavelength (G) on the basis of the third baseline intensity (G), the second baseline intensity (R), the third measurement intensity (G), the second measurement intensity (R), the third information, and the fourth information.

When the absorbance at only either of the wavelengths B and G is used, a calibration curve corresponding to the absorbance may be used. Calculating the absorbance ratio by using, when possible, both of the absorbances at the wavelengths G and B will increase the accuracy because noise that could occur due to a variation in the amount of the culture solution or a variation in the concentration of the pH indicator can be canceled.

When the calculation of absorbances of the pH indicator is finished, the pH of the culture solution CL is calculated from the absorbance ratio of the pH indicator (step S15). In this case, the control apparatus 30 calculates the pH of the culture solution CL on the basis of the absorbance of the pH indicator at the wavelength B and the absorbance of the pH indicator at the wavelength G. More specifically, the control apparatus 30 calculates the common logarithm of the ratio between the absorbance at the wavelength B and the absorbance at the wavelength G and substitutes the calculated common logarithm into the linear function specified in step S5, so as to calculate the pH of the culture solution.

When the pH of the culture solution CL is calculated, the control apparatus 30 displays the calculated pH on the display apparatus (step S16). In this case, the control apparatus 30 outputs an image indicating the history of the pH of the culture solution CL to the display apparatus, and the display apparatus displays a screen including the image indicating the history of the pH of the culture solution CL. For example, the control apparatus 30 may display a screen 35a on the display apparatus. The screen 35a includes a graph G1 constituted by an image indicating the history of the density of cells, a graph G2 constituted by an image indicating the history of the number of cells, and a graph G3 constituted by an image indicating the history of the pH of the culture solution CL. The screen 35a also includes an image M indicating which of the wells of the culture container C1 information is being displayed for. In addition to the history of the pH, the graph G3 may include information on a pH range appropriate for culturing. Thus, by observing the graph G3, the user can determine at first sight whether the pH of the culture solution CL falls within the appropriate range.

Afterward, the control apparatus 30 determines whether the culture solution CL should be replaced (step S17). In this case, the control apparatus 30 may determine whether the culture solution CL should be replaced on the basis of the pH of the culture solution CL or a growing state such as the number or density of cells. When determining that the culture solution CL does not need to be replaced, the control apparatus 30 returns to step S12 and repeats the above processes. When determining that the culture solution CL should be replaced, the control apparatus 30 encourages the user to replace the culture solution CL by, for example, displaying an alert on the display apparatus. When the replacement of the culture solution CL is encouraged, the user replaces the culture solution CL (step S18) and then causes the system 1 to resume the culture monitoring.

As described above, even when the wavelength intensity ratio of the light source 14 varies during a culture period, the system 1 in accordance with the present embodiment allows the absorbance of a pH indicator to be stably measured with sufficient accuracy during the culture period. Thus, the pH of the culture solution CL can be continuously measured with high accuracy. The system 1 can measured the pH of a culture solution by using the configuration for acquiring an image of a sample S. Hence, the above effect can be attained without changing the exiting apparatus configuration. The system 1 does not need a complicated circuit for stabilizing the output of the light source 14, so the cost for the apparatus can be reduced. The system 1 allows examinations to be performed within the incubator 20, thereby reducing a risk of occurrence of contamination.

Figure 12:
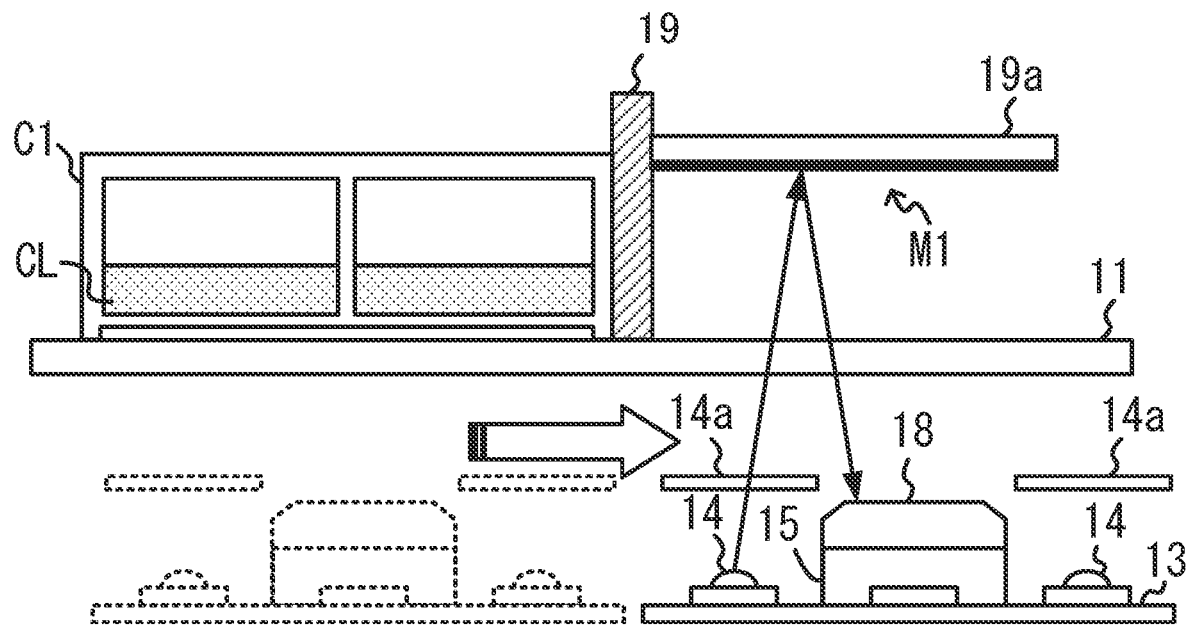
FIG. 12 illustrates a variation of an image capturing apparatus 10.
Figure 13:
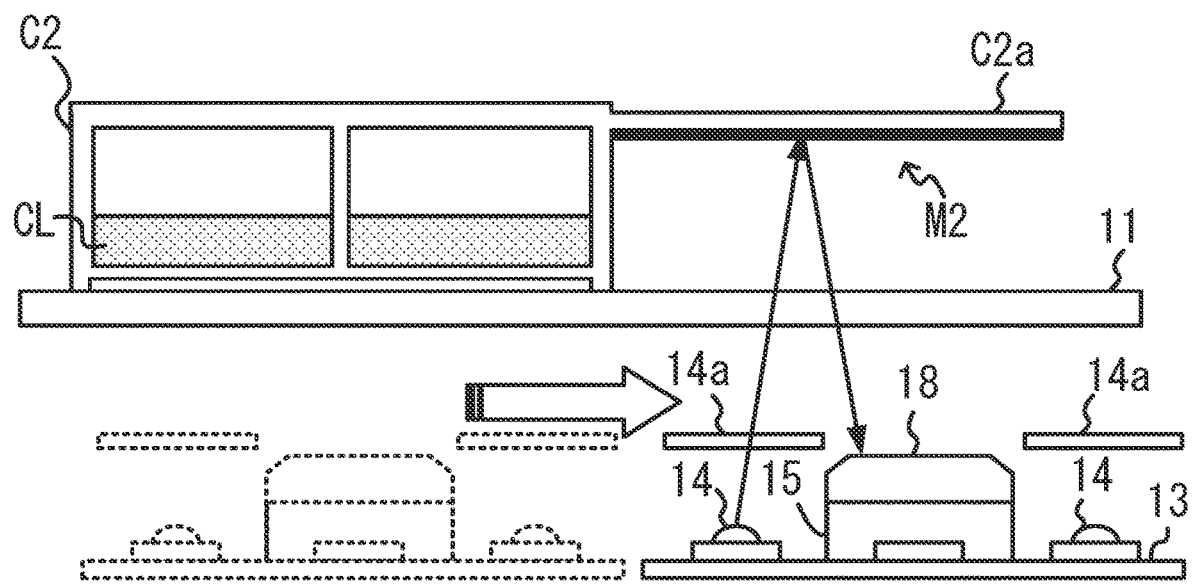
FIG. 13 illustrates another variation of an image capturing apparatus 10.

In the example presented above, the system 1 obtains light source information on the basis of the intensity of light reflected by the reflection member 17. However, this example is not the only method for obtaining light source information. For example, a reflection surface M1 may be provided, as depicted in FIG. 12, on a protruding section 19a of a container holder 19 installed on the placement surface 11 so as to hold the culture container C1 at a predetermined position, and light source information may be obtained on the basis of the intensity of light reflected by the reflection surface M1. Alternatively, a culture container C2 provided with a protruding section C2a on which a reflection surface M2 is formed may be used as depicted in FIG. 13, and light source information may be obtained on the basis of the intensity of light reflected by the reflection surface M2. In each of FIGS. 12 and 13, the reflection surface and the top of the container are provided at almost the same height. In the examination method, however, the height of the reflection surface is not limited because a variation in an absorbance caused by a variation in the optical path length is corrected. When providing a reflection plate independently of the culture container C1, the height of the reflection plate may be freely set.

Second Embodiment

Figure 14:
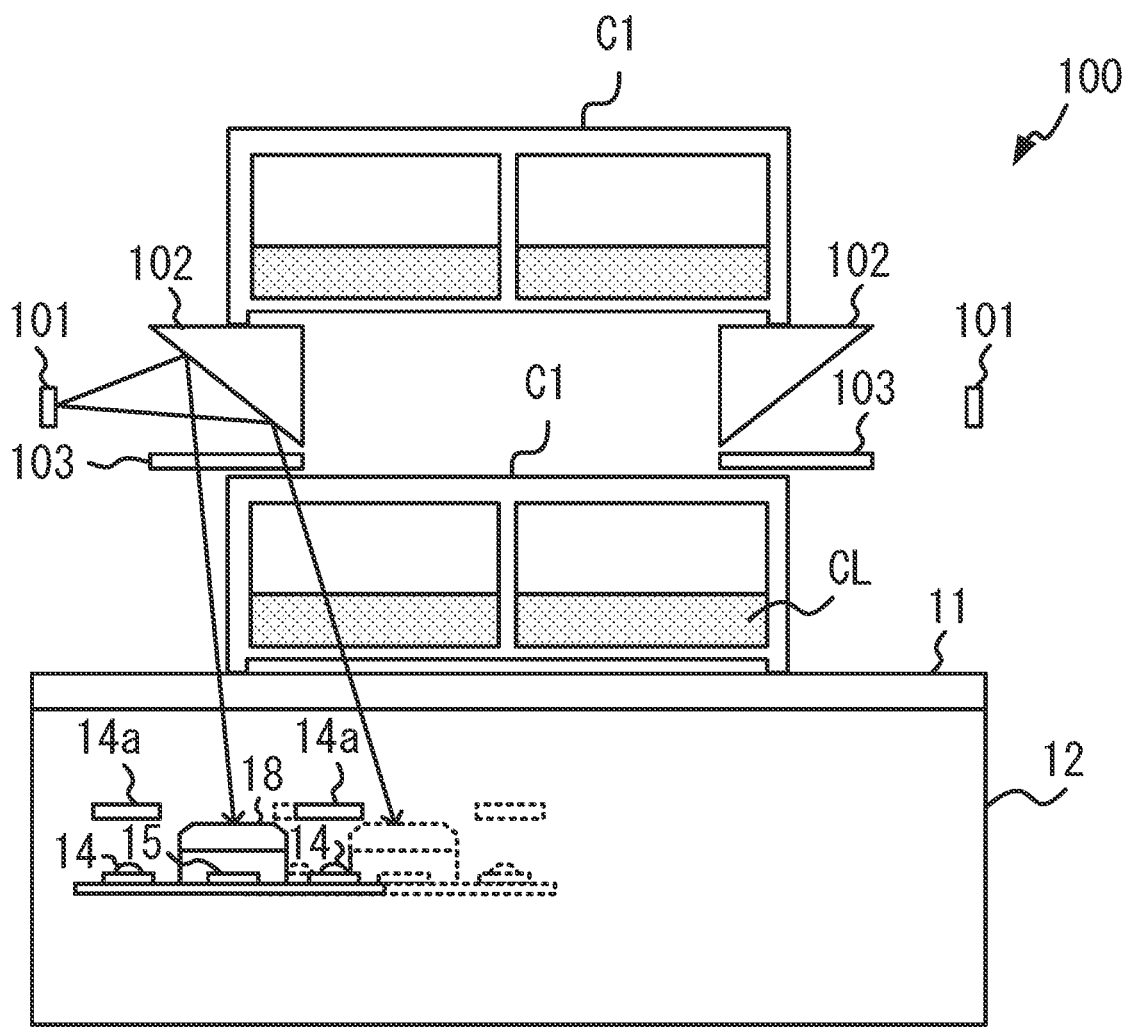
FIG. 14 is a schematic cross-sectional view illustrating the configuration of an image capturing apparatus 100.
Figure 15:
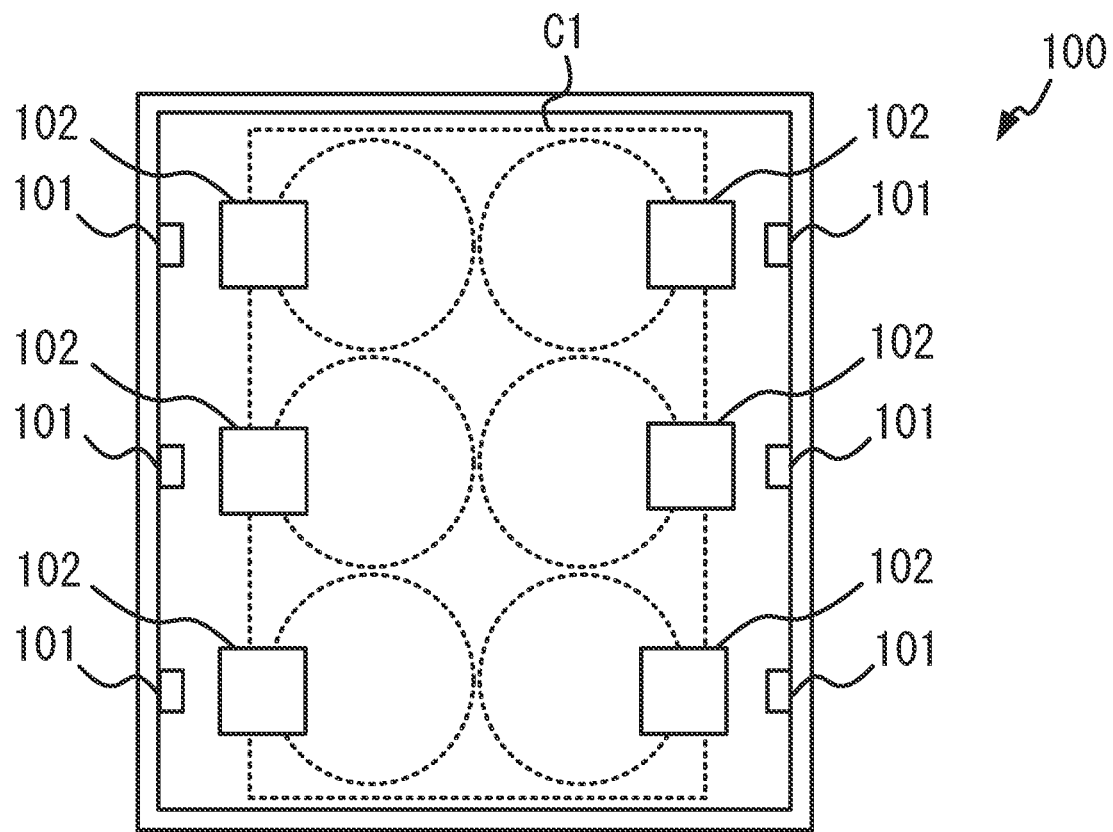
FIG. 15 is a schematic top view illustrating the configuration of an image capturing apparatus 100.

FIG. 14 is a schematic cross-sectional view illustrating the configuration of an image capturing apparatus 100. FIG. 15 is a schematic top view illustrating the configuration of the image capturing apparatus 100. The system in accordance with the present embodiment is different from the system 1 in that the image capturing apparatus 100 depicted in FIGS. 14 and 15 is provided in place of the image capturing apparatus 10. Otherwise, the system in accordance with the present embodiment is similar to the system 1.

The image capturing apparatus 100 is different from the image capturing apparatus 10 in that light sources 101, reflection members 102, and diffuser panels 103 are provided. The light sources 101 are disposed outward of a region obtained by upwardly extending the region of an image projected onto the placement surface of a culture container CL placed on the placement surface 11. That is, the light sources 101 are disposed outward of the space above the culture container CL. In other words, the light sources 101 are disposed outward of the space between two stacked culture containers CL. The reflection member 102 is a deflection element that deflects emitted light from the light source 101 toward the image pickup element 15. The diffuser panel 103 is a light diffusion element disposed between the light source 101 and the image pickup element 15. In the system in accordance with the present embodiment, emitted light from the light source 101 is detected by the image pickup element 15 provided within the housing 12 so as to measure the absorbance of the pH indicator and the pH of the culture solution CL.

In the image capturing apparatus 100, the light sources 101, the reflection members 102, and the diffuser panels 103 are fixed at higher positions than the placement surface 11. At least the reflection members 102 and the diffuser panels 103 are fixed at higher positions than the upper surface of the culture container C1 placed on the placement surface 11. Emitted light from the light source 101 is reflected by the reflection member 102, diffused by the diffuser panel 103, and then passes the inside and outside of the culture container C1. By moving the image pickup element 15, the image capturing apparatus 100 can selectively detect light that has passed the inside of the culture container C1 and light that has passed the outside of the culture container C1.

The reflection member 102 is also used as a support member for supporting a culture container C1. Thus, a plurality of culture containers C1 can be disposed above the image capturing apparatus 100. Hence, the image capturing apparatus 100 allows the limited space within the incubator 20 to be used effectively. By using the reflection member 102, a sufficient length of optical path from the light source 101 to the diffuser panel 103 can be ensured without providing the light source 101 at an excessively high position. Hence, the image capturing apparatus 100 can be configured to be compact.

As with the system 1, the system in accordance with the present embodiment can examine the culture solution CL by performing the processes indicted in FIG. 7. Moreover, even when the wavelength intensity ratio of the light source 101 varies during a culture period, the system in accordance with the present embodiment allows the absorbance of a pH indicator to be stably measured with sufficient accuracy during the culture period.

Third Embodiment

Figure 16:
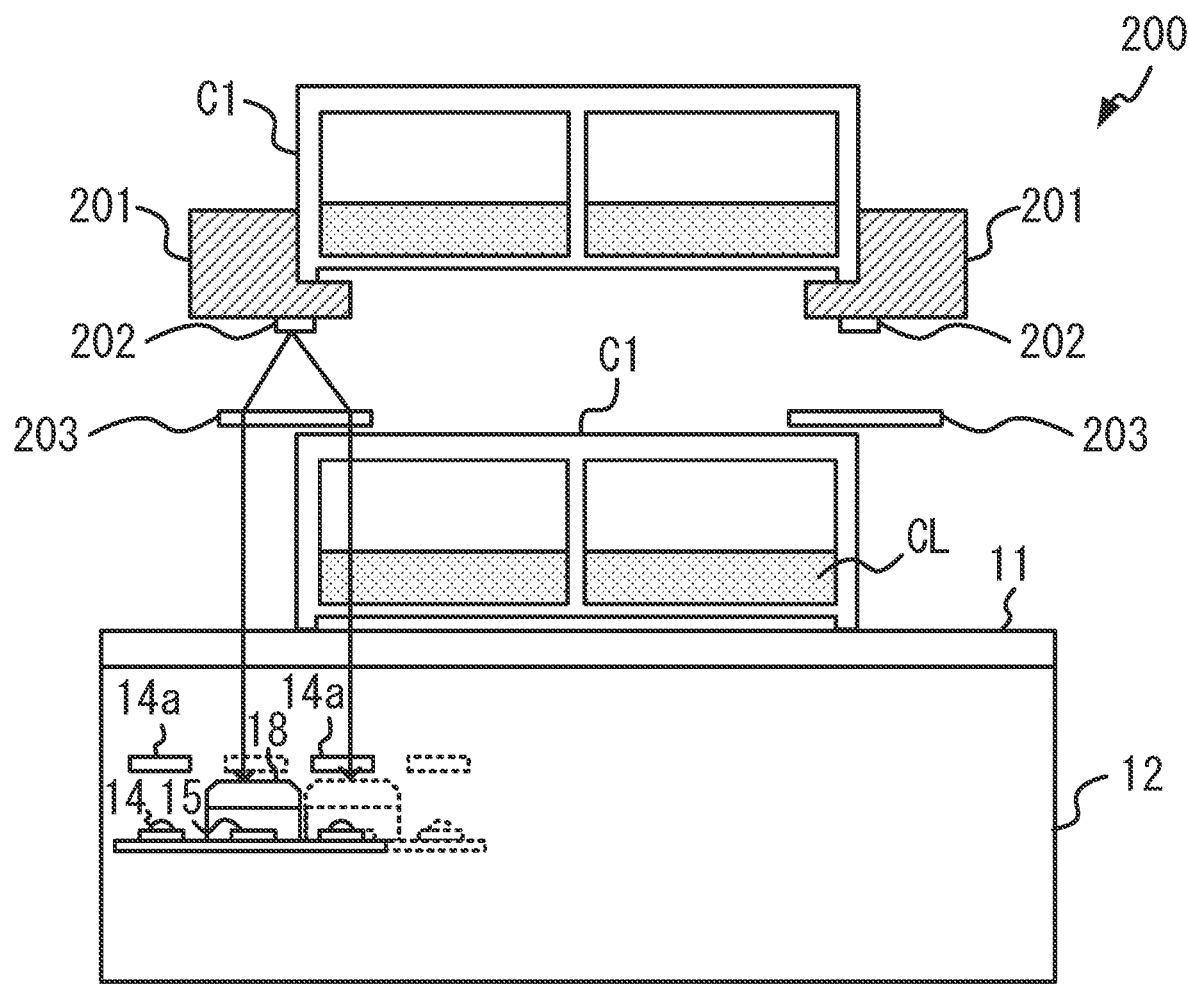
FIG. 16 is a schematic cross-sectional view illustrating the configuration of an image capturing apparatus 200.

FIG. 16 is a schematic cross-sectional view illustrating the configuration of an image capturing apparatus 200. The system in accordance with the present embodiment is different from the system 1 in that the image capturing apparatus 200 depicted in FIG. 16 is provided in place of the image capturing apparatus 10. Otherwise, the system in accordance with the present embodiment is similar to the system 1.

The image capturing apparatus 200 is different from the image capturing apparatus 10 in that support members 201 for supporting a culture container C1, light sources 202, and diffuser panels 203 are provided. The light source 202 is installed on the lower surface of the support member 201. The diffuser panel 203 is a light diffusion element disposed between the light source 202 and the image pickup element 15. In the system in accordance with the present embodiment, emitted light from the light source 202 is detected by the image pickup element 15 provided within the housing 12 so as to measure the absorbance of the pH indicator and the pH of the culture solution CL.

In the image capturing apparatus 200, the support members 201, the light sources 202, and the diffuser panels 203 are fixed at higher positions than the placement surface 11 and the upper surface of the culture container C1 placed on the placement surface 11. Emitted light from the light source 202 is diffused by the diffuser panel 203 and then passes the inside and outside of the culture container C1. By moving the image pickup element 15, the image capturing apparatus 200 can selectively detect light that has passed the inside of the culture container C1 and light that has passed the outside of the culture container C1.

As with the system 1, the system in accordance with the present embodiment can examine the culture solution CL by performing the processes indicted in FIG. 7. Moreover, even when the wavelength intensity ratio of the light source 202 varies during a culture period, the system in accordance with the present embodiment allows the absorbance of a pH indicator to be stably measured with sufficient accuracy during the culture period.

The embodiments described above indicate specific examples to facilitate understanding of the invention, and the present invention is not limited to these embodiments.

Some of the embodiments described above may be applied to other embodiments. Various modifications or changes can be made to the examination method, the system, and the computer-readable medium without departing from the recitation in the claims.

Figure 17:
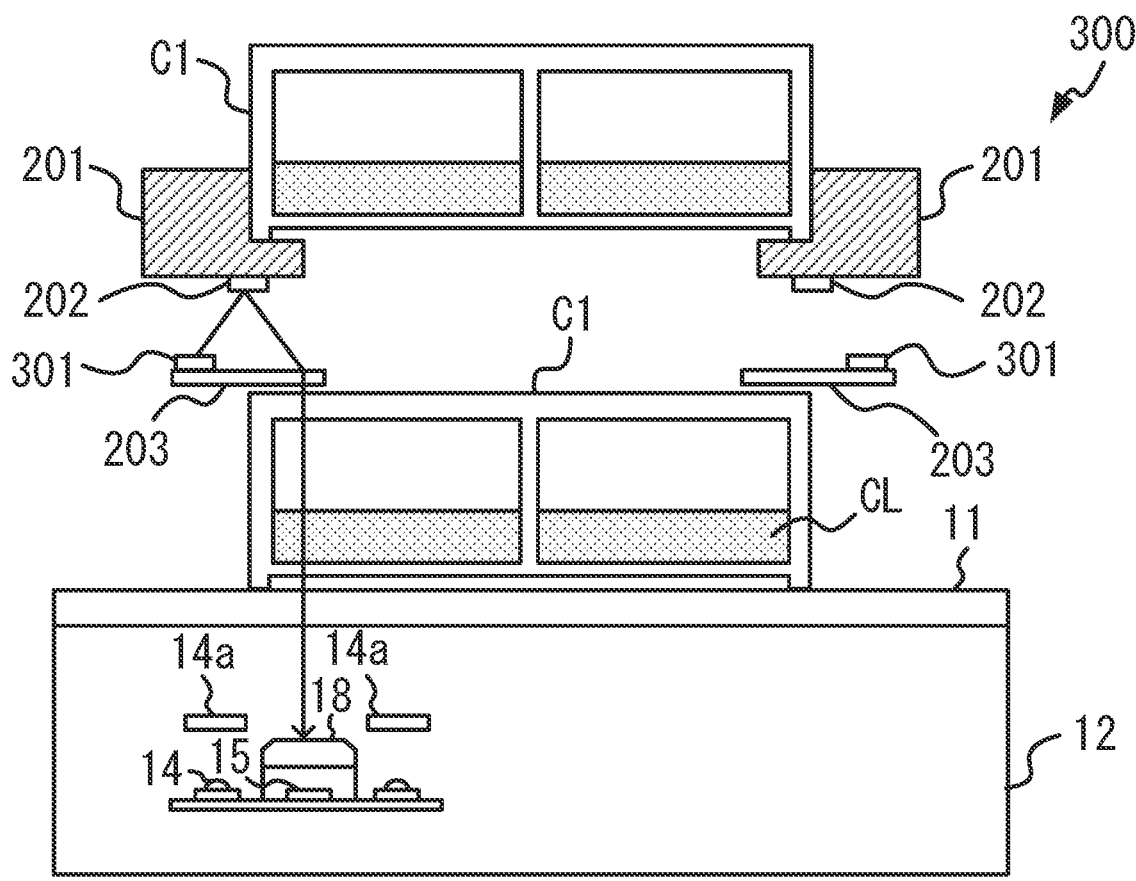
FIG. 17 is a schematic cross-sectional view illustrating the configuration of an image capturing apparatus 300.
Figure 18:
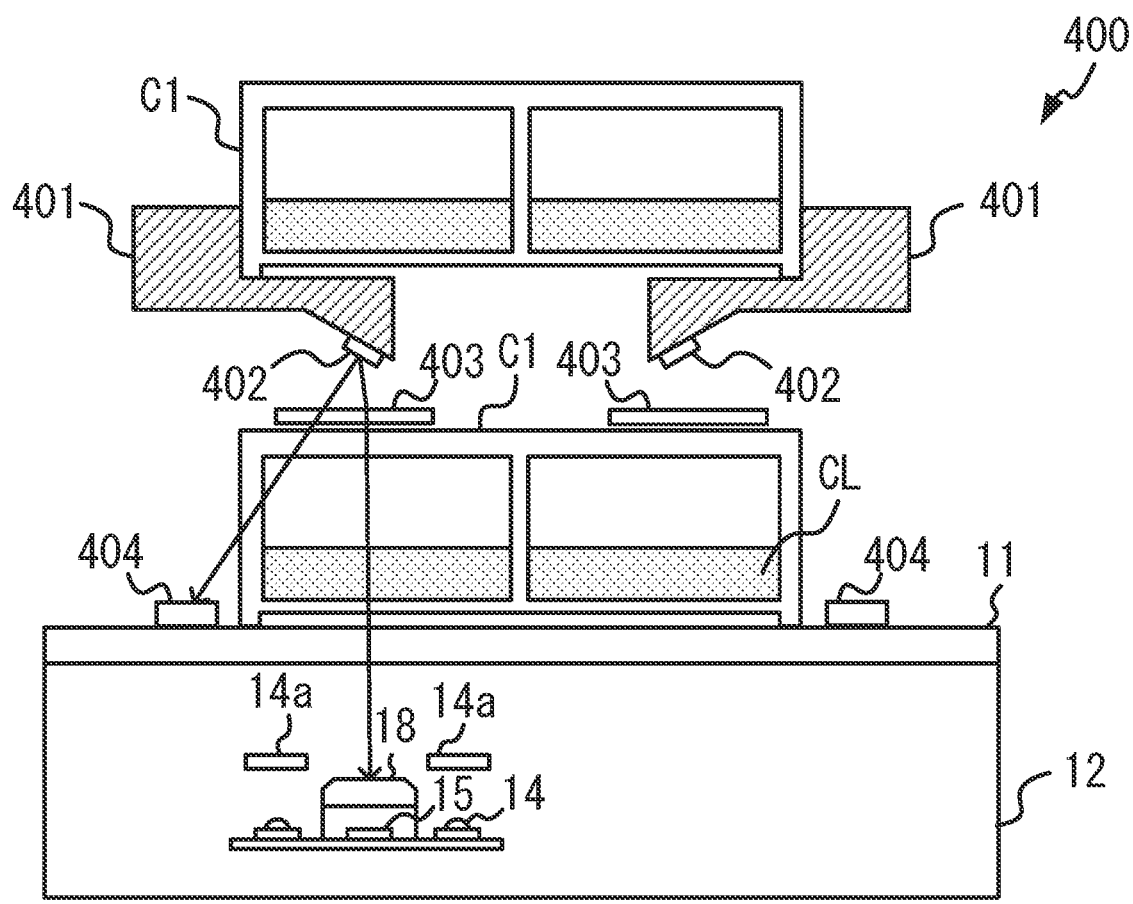
FIG. 18 is a schematic cross-sectional view illustrating the configuration of an image capturing apparatus 400.
Figure 19:
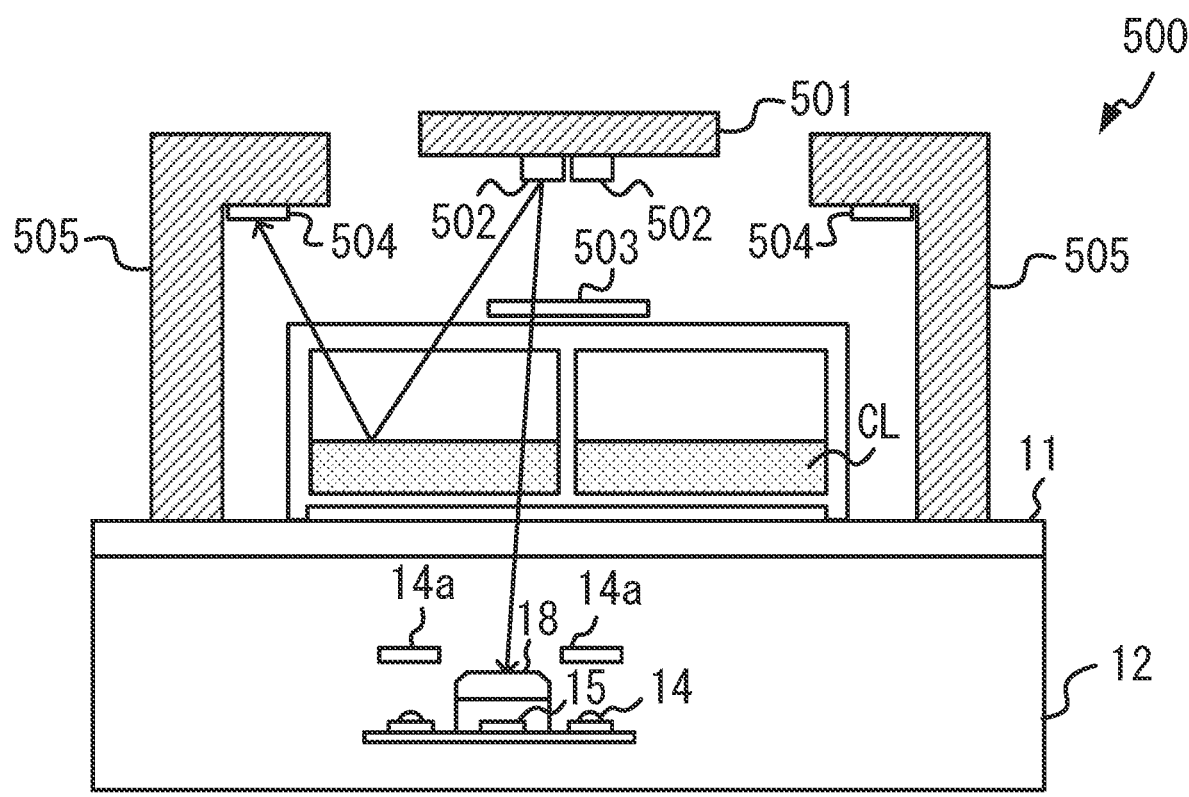
FIG. 19 is a schematic cross-sectional view illustrating the configuration of an image capturing apparatus 500.

In the examples indicated for the above-described embodiments, the image pickup element 15 that acquires an image of a sample S is used to measure an absorbance and a pH. However, as indicated in FIGS. 17-19, the image capturing apparatus may include a second photodetector in addition to the image pickup element 15, and an absorbance and a pH may be measured using the image pickup element 15 and the second photodetector. The second photodetector may be disposed at a second position on which light that is a portion of emitted light from the light source and does not pass through the culture container C1 is incident. For example, the second photodetector may be a light quantity sensor such as a photodiode installed in the vicinity of the light source so as to measure the quantity of emitted light from the light source. The second photodetector may be configured to acquire light that does not pass through the culture solution CL but passes an empty space within the culture container C1. When the second photodetector is provided, light source information may be obtained on the basis of the intensity of light measured by the second photodetector when measuring a baseline intensity and the intensity of light measured by the second photodetector when measuring a measurement intensity. By using the second photodetector, a baseline intensity and an auxiliary baseline intensity can be concurrently measured. In addition, by using the second photodetector, a measurement intensity and an auxiliary measurement intensity can be concurrently measured.

An image capturing apparatus 300 depicted in FIG. 17 is different from the image capturing apparatus 200 in that photodiodes 301 are provided. By using the photodiode 301, the image capturing apparatus 300 can measure an auxiliary measurement intensity and an auxiliary baseline intensity. The photodiode 301 is fixed to the diffuser panel 203 and may be disposed at a position on which light that does not pass through the culture solution CL is incident. In the image capturing apparatus 300, emitted light from the light source 202 is incident directly on the photodiode 301, but light emitted from the light source 202 and deflected by a mirror or the like may be incident on the photodiode 301. As with the system 1, the system provided with the image capturing apparatus 300 allows the absorbance of a pH indicator to be stably measured with sufficient accuracy during a culture period.

An image capturing apparatus 400 depicted in FIG. 18 is different from the image capturing apparatus 200 in that support members 401 for supporting a culture container C1, light sources 402, diffuser panels 403, and photodiodes 404, i.e., second photodetectors, are provided in place of the support members 201, the light sources 202, and the diffuser panels 203. In the examples indicated for the above-described embodiments, the image capturing apparatuses measure an auxiliary baseline intensity and an auxiliary measurement intensity by detecting light that does not pass through the culture container C1. In this regard, the image capturing apparatus 400 is different from the image capturing apparatuses described above in that the image capturing apparatus 400 measures an auxiliary baseline intensity and an auxiliary measurement intensity on the basis of light that passes through the culture container C1 without passing through the culture solution CL. When light passes through wall surfaces of the culture container C1 as in the present embodiment, the culture container desirably has flat side surfaces.

In the image capturing apparatus 400, a portion of emitted light from the light source 402 fixed to the support member 401 enters the culture container C1 through the upper surface of the culture container C1 after passing through the diffuser panel 403. Then, the light that has entered the culture container C1 travels to the outside of the culture container C1 through a side surface thereof without reaching the culture solution CL, and is incident on the photodiode 404 disposed on the placement surface 11. Hence, by using the photodiode 404, the image capturing apparatus 400 can measure an auxiliary measurement intensity and an auxiliary baseline intensity. Accordingly, as with the system 1, the system provided with the image capturing apparatus 400 allows the absorbance of a pH indicator to be stably measured with sufficient accuracy during a culture period.

An image capturing apparatus 500 depicted in FIG. 19 is different from the image capturing apparatus 200 in that a support member 501, light sources 502, a diffuser panel 503, photodiodes 504, i.e., second photodetectors, and support members 505 are provided in place of the support members 201, the light sources 202, and the diffuser panels 203. The image capturing apparatus 500 is similar to the image capturing apparatus 400 in that the image capturing apparatus 500 measures an auxiliary baseline intensity and an auxiliary measurement intensity on the basis of light that passes through the culture container C1 without passing through the culture solution CL. However, the image capturing apparatus 500 is different from the image capturing apparatus 400 in that the image capturing apparatus 500 measures an auxiliary baseline intensity and an auxiliary measurement intensity on the basis of light reflected by the liquid surface of the culture solution CL. In the meantime, light reflected by a lid section of the culture container may be used in addition to the light reflected by the liquid surface of the culture solution CL. When a microwell plate is used, light reflected by a non-well portion of the microwell plate may be used.

In the image capturing apparatus 500, a portion of emitted light from the light source 502 fixed to the support member 501 enters the culture container C1 through the upper surface of the culture container C1 without passing through the diffuser panel 503. Then, the light that has entered the culture container C1 without passing through the diffuser panel 503 is Fresnel reflected by the liquid surface of the culture solution CL and is incident on the photodiode 504. Hence, by using the photodiode 504, the image capturing apparatus 500 can measure an auxiliary measurement intensity and an auxiliary baseline intensity. Accordingly, as with the system 1, the system provided with the image capturing apparatus 500 allows the absorbance of a pH indicator to be stably measured with sufficient accuracy during a culture period.

Although FIG. 19 depicts the example in which Fresnel reflection occurs on the liquid surface of the culture solution, the second photodetector may detect light Fresnel reflected by the upper surface of the culture container C1.

The image capturing apparatus may be separated from the photodetector. In particular, the second photodetector may be installed on an upper portion of the culture container and obtain light source information by receiving light reflected by the surface of the culture solution. The second photodetector may be installed on a side surface of the culture container and configured to receive light passing an empty space within the culture container C1 without passing through the culture solution CL.

Figure 20:
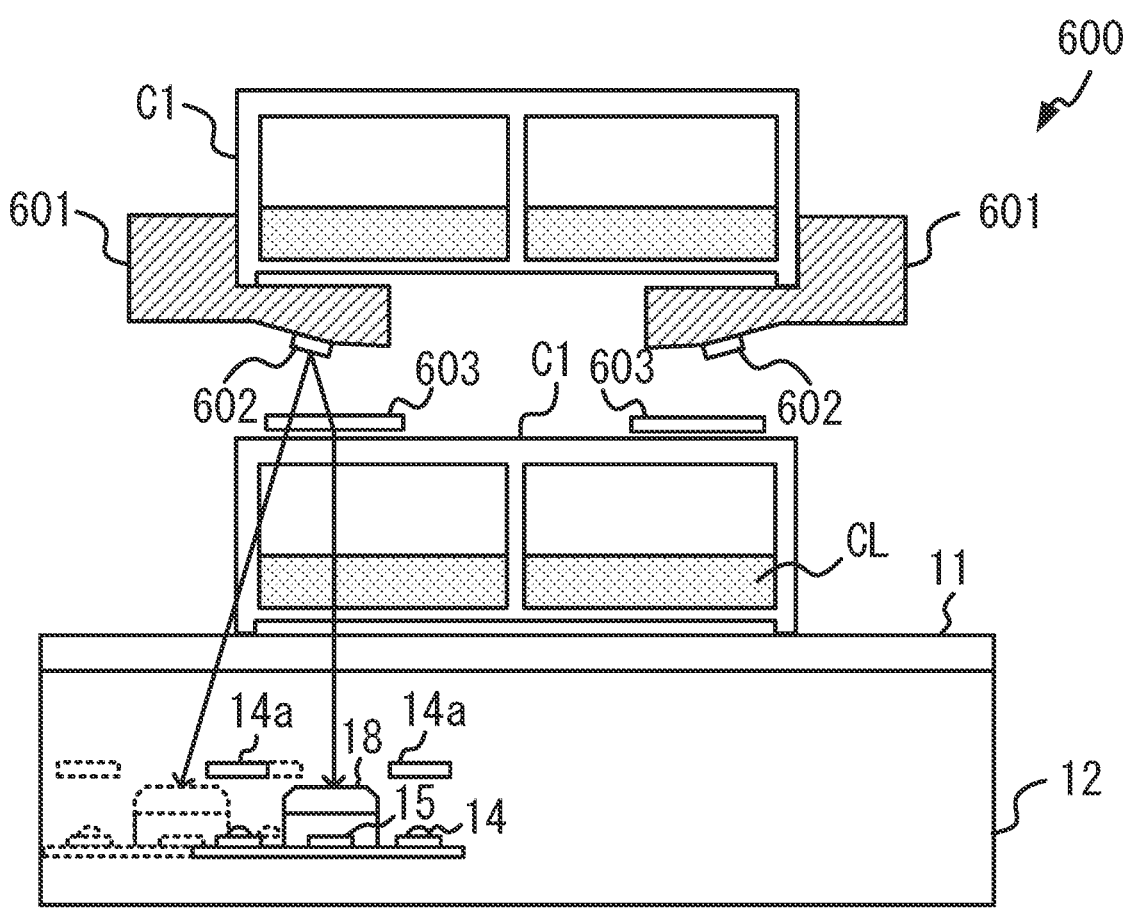
FIG. 20 is a schematic cross-sectional view illustrating the configuration of an image capturing apparatus 600.

FIG. 18 depicts the example in which the second photodetector detects light passing through the culture container C1 without passing through the culture solution CL. However, as depicted in FIG. 20, the image pickup element 15 may detect light passing through the culture container C1 without passing through the culture solution CL. An image capturing apparatus 600 depicted in FIG. 20 is different from the image capturing apparatus 400 in that support members 601, light sources 602, and diffuser panels 603 are provided in place of the support members 401, the light sources 402, and the diffuser panels 403, and in that the photodiodes 404, i.e., second photodetectors, are not provided. In the image capturing apparatus 600, light passing through the culture container C1 without passing through the culture solution C is detected by the image pickup element 15 by moving the stage 13. Thus, by using the image pickup element 15, the image capturing apparatus 600 measures an auxiliary measurement intensity and an auxiliary baseline intensity. As with the system 1, the system provided with the image capturing apparatus 600 allows the absorbance of a pH indicator to be stably measured with sufficient accuracy during a culture period. When a microwell plate is used, light that has passed through a non-well portion of the microwell plate may be received, instead of light passing through the culture container C1 without passing through the culture solution CL.

In the examples indicated for the above-described embodiments, the diffuser panel and the deflection member are used to cause emitted light from the light source to pass both the inside and outside of the culture container C1. However, the light source may be of a surface-emitting type so as to implement a wide illumination range without using such elements. Especially, if a point light source is used in the third embodiment, the light source needs to be fixed at a certain height so as to ensure an illumination range, and thus the efficiency of use of the space in the incubator 20 tends to be limited. Using a surface-emitting light source can further improve the efficiency of use.

In the examples indicated for the above-described embodiments, the light source performs wavelength switching to sequentially emit light rays having a plurality of wavelengths. However, the light source may be a white light source. Optical filters (e.g., bandpass filters) having different transparent wavelength bands may be set in the optical path in turn so as to selectively detect light rays having particular wavelengths from emitted light from the light source. Alternatively, an image pickup element provided with color filters may be used to concurrently detect light rays having a plurality of wavelengths. In this case, the time required for examination can be reduced.

When a CMOS sensor is used for the image pickup element, the light reception region may be divided into a region for detecting an auxiliary measurement intensity and a region for detecting a measurement intensity, so that both an auxiliary measurement intensity and a measurement intensity can be concurrently measured when light is emitted once. In this case, these measurements can be performed without moving the image pickup element and the deflection element.

In the examples indicated for the embodiments described above, a schedule is set for the examination of a culture solution. However, the timings at which the culture solution is examined may be decided on by the user as necessary. The culture solution may be examined when the user thinks that there may be an abnormality therein.

In the examples indicated for the embodiments described above, a measurement intensity is measured, and then an auxiliary measurement intensity is measured. However, the order in which these intensities are measured is not particularly limited. A measurement intensity may be measured after an auxiliary measurement intensity is measured, or a measurement intensity and an auxiliary measurement intensity may be concurrently measured.

An aspect of the embodiments described above can provide the following system.

A system comprising:
 an image capturing apparatus that has a culture container placed thereon and captures an image of a sample cultured within the culture container; and
 a control apparatus that controls the image capturing apparatus, wherein
 the image capturing apparatus includes
  a light source,
  a photodetector for detecting emitted light from the light source,
  a deflection element (reflection member) for deflecting the emitted light from the light source toward the photodetector,
  a light diffusion element (diffuser panel) disposed between the light source and the photodetector, and
  a housing having a placement surface on which the culture container is placed,
 the photodetector is provided within the housing,
 the light source, the deflection element, and the light diffusion element are fixed at higher positions than the placement surface, and
 the control apparatus
  moves the photodetector to a first position on which light that is a portion of emitted light from the light source and has passed through the culture container is incident,
  when the photodetector is located at the first position, measures, as a measurement intensity by using the photodetector, an intensity of light that is a portion of emitted light from the light source and has passed through a culture solution containing the pH indicator and the culture container,
  moves the photodetector to a second position on which light that is a portion of emitted light from the light source and does not pass through the culture container is incident,
  obtains light source information on the basis of an intensity of light measured by the photodetector at the second position, and
  calculates an absorbance of the pH indicator on the basis of the measurement intensity and the light source information.

In this configuration, the light source, the deflection element, and the light diffusion element are fixed at higher positions than the placement surface. At least the deflection element and the light diffusion element are fixed at higher positions than the upper surface of the culture container placed on the placement surface. The light source is disposed outward of a region obtained by upwardly extending the region of an image projected onto the placement surface of the culture container placed on the placement surface. The light source and the deflection member may be arranged in the horizontal direction.

In accordance with such a configuration, the image capturing apparatus can be configured to be compact in the height direction.

What is claimed is:

1. A method for examining a culture solution containing a pH indicator and accommodated in a culture container, the method comprising:
    causing a processor of a control apparatus to control one or more photodetectors to:
        measure, as a baseline intensity, an intensity of light that is a portion of emitted light from a light source and has passed through a solution not containing the pH indicator and the culture container;
        measure, as an auxiliary baseline intensity, an intensity of light that is a portion of emitted light from the light source and does not pass through the solution;
        after measuring the baseline intensity and the auxiliary baseline intensity, measure, as a measurement intensity, an intensity of light that is a portion of emitted light from the light source and has passed through the culture solution containing the pH indicator and the culture container; and
        after measuring the baseline intensity and the auxiliary baseline intensity, measure, as an auxiliary measurement intensity, an intensity of light that is a portion of emitted light from the light source and does not pass through the culture solution; and
    on the basis of the baseline intensity, the auxiliary baseline intensity, the measurement intensity, and the auxiliary measurement intensity, calculating an absorbance of the pH indicator at at least one wavelength included in emitted light from the light source.

2. The method according to claim 1,
    wherein causing the processor to control the one or more photodetectors to measure the baseline intensity comprises controlling the one or more photodetectors to:
        measure, as a first baseline intensity, an intensity of light that has passed through the solution and the culture container, and has a first wavelength at which the absorbance of the pH indicator is pH-dependent; and
        measure, as a second baseline intensity, an intensity of light that has passed through the solution and the culture container and has a second wavelength at which the absorbance of the pH indicator is not pH-dependent,
    wherein causing the processor to control the one or more photodetectors to measure the measurement intensity comprises controlling the one or more photodetectors to:
        measure, as a first measurement intensity, an intensity of light that has the first wavelength and has passed through the culture solution and the culture container; and
        measure, as a second measurement intensity, an intensity of light that has the second wavelength and has passed through the culture solution and the culture container,
    wherein causing the processor to control the one or more photodetectors to measure the auxiliary baseline intensity comprises controlling the one or more photodetectors to measure, as the auxiliary baseline intensity, the intensity of the light from the light source that has the first wavelength and the intensity of the light from the light source that has the second wavelength when measuring the baseline intensity,
    wherein causing the processor to control the one or more photodetectors to measure the auxiliary measurement intensity comprises controlling the one or more photodetectors to measure, as the auxiliary baseline intensity, the intensity of the light from the light source that has the first wavelength and the intensity of the light from the light source that has the second wavelength when measuring the baseline intensity, and
    wherein calculating the absorbance of the pH indicator comprises calculating the absorbance of the pH indicator at the first wavelength on the basis of the first baseline intensity, the second baseline intensity, the first measurement intensity, the second measurement intensity, the auxiliary baseline intensity and the auxiliary measurement intensity.

3. The method according to claim 2,
    wherein causing the processor to control the one or more photodetectors to measure the baseline intensity comprises controlling the one or more photodetectors to measure, as a third baseline intensity, an intensity of light that has passed through the solution and the culture container, and has a third wavelength at which the absorbance of the pH indicator is pH-dependent, the third wavelength being different from the first wavelength,
    wherein causing the processor to control the one or more photodetectors to measure the measurement intensity comprises controlling the one or more photodetectors to measure, as a third measurement intensity, an intensity of the light from the light source that has the third wavelength and has passed through the culture solution and the culture container,
    wherein causing the processor to control the one or more photodetectors to measure the auxiliary baseline intensity comprises controlling the one or more photodetectors to measure, as the auxiliary baseline intensity, an intensity of the light from the light source that has the third wavelength and an intensity of the light from the light source that has the second wavelength when measuring the baseline intensity,
    wherein causing the processor to control the one or more photodetectors to measure the auxiliary measurement intensity comprises controlling the one or more photodetectors to measure, as the auxiliary measurement intensity, the intensity of the light from the light source that has the third wavelength and the intensity of the light from the light source that has the second wavelength when measuring the measurement intensity,
    wherein method further comprises calculating an absorbance of the pH indicator at the third wavelength on the basis of the third baseline intensity, the second baseline intensity, the third measurement intensity, the second measurement intensity, the auxiliary baseline intensity and the auxiliary measurement intensity,
    wherein calculating the absorbance of the pH indicator further comprises calculating the absorbance of the pH indicator at the third wavelength on the basis of the third baseline intensity, the second baseline intensity, the third measurement intensity, the second measurement intensity, the third information, and the fourth information, and
    wherein the method further comprises calculating a pH of the culture solution on the basis of the absorbance of the pH indicator at the first wavelength and the absorbance of the pH indicator at the third wavelength.

4. The method according to claim 3,
    wherein the calculating the absorbance of the pH indicator further comprises:
        calculating the absorbance of the pH indicator for the first wavelength based on:

a ratio that is attained when measuring an intensity of light of the first wavelength of the auxiliary baseline intensity and an intensity of light of the second wavelength of the auxiliary baseline intensity; and
a ratio that is attained when measuring an intensity of light of the first wavelength of the auxiliary measurement intensity and an intensity of light of the second wavelength of the auxiliary measurement intensity.

5. The method according to claim 4,
wherein the calculating the absorbance of the pH indicator further comprises:
calculating the absorbance of the pH indicator for the third wavelength based on:
a ratio that is attained when measuring an intensity of light of the third wavelength of the auxiliary baseline intensity and an intensity of light of the second wavelength of the auxiliary baseline intensity; and
a ratio that is attained when measuring an intensity of light of the third wavelength of the auxiliary measurement intensity and an intensity of light of the second wavelength of the auxiliary measurement intensity.

6. A system comprising:
an image capturing apparatus configured to have a culture container placed thereon and to capture an image of a sample cultured within the culture container; and
a control apparatus configured to control the image capturing apparatus,
wherein the image capturing apparatus comprises:
a light source; and
one or more photodetectors, and
wherein the control apparatus is configured to control the one or more photodetectors to:
measure, as a baseline intensity, an intensity of light that is a portion of emitted light from the light source and has passed through a solution not containing a pH indicator and the culture container;
measure, as an auxiliary baseline intensity, an intensity of light that is a portion of emitted light from the light source and does not pass through the solution;
after measuring the baseline intensity and the auxiliary baseline intensity, measure, as a measurement intensity, an intensity of light that is a portion of emitted light from the light source and has passed through a culture solution containing the pH indicator and the culture container; and
after measuring the baseline intensity and the auxiliary baseline intensity, measure, as an auxiliary measurement intensity, an intensity of light that is a portion of emitted light from the light source and does not pass through the culture solution; and
wherein the control apparatus is configured to, on the basis of the baseline intensity, the auxiliary baseline intensity, the measurement intensity, and the auxiliary measurement intensity, calculate an absorbance of the pH indicator at at least one wavelength included in emitted light from the light source.

7. The system of claim 6,
wherein the control apparatus is configured to control a display apparatus to display information indicating a history of the pH of the culture solution.

8. The system of claim 6,
wherein the control apparatus is configured to:
control a drive mechanism to move the one or more photodetectors to a first position on which light that is a portion of emitted light from the light source and has passed through the culture container is incident;
control the one or more photodetectors to measure the baseline intensity and the measurement intensity at the first position;
control the drive mechanism to move the one or more photodetectors to a second position on which light that is a portion of emitted light from the light source and does not pass through the culture solution is incident; and
control the one or more photodetectors to measure the auxiliary baseline intensity and the auxiliary measurement intensity at the second position.

9. The system of claim 8,
wherein the image capturing apparatus further comprises a housing having a placement surface on which the culture container is placed,
wherein the one or more photodetectors and the light source are provided within the housing, and
wherein the light source is configured to move together with the one or more photodetectors within the housing.

10. The system of claim 8,
wherein the image capturing apparatus further comprises a housing having a placement surface on which the culture container is placed,
wherein the one or more photodetectors are provided within the housing, and
wherein the light source is fixed at a higher position than the placement surface.

11. The system of claim 10,
wherein the image capturing apparatus further comprises a deflection element configured to deflect emitted light from the light source toward the one or more photodetectors.

12. The system of claim 10,
wherein the image capturing apparatus further comprises a light diffusion element between the light source and the one or more photodetectors.

13. The system of claim 10,
wherein the light source is disposed outward of a region obtained by upwardly extending a region of an image projected onto the culture container placed on the placement surface.

14. The system of claim 6,
wherein the image capturing apparatus is configured to capture an image of the sample on the basis of light that is a portion of emitted light from the light source and has been detected by the one or more photodetectors.

15. The system of claim 6,
wherein the image capturing apparatus is configured to capture an image of the sample on the basis of light detected by the photodetector.

16. The system of claim 6,
wherein the one or more photodetectors comprise:
a first photodetector disposed at a first position on which light that is a portion of emitted light from the light source and passes through the culture solution is incident; and
a second photodetector disposed at a second position on which light that is a portion of emitted light from the light source and does not pass through the culture solution is incident, the second photodetector being different from the first photodetector, and wherein the control apparatus is configured to control the first photodetector to measure the measurement intensity, and wherein the control apparatus is configured to control the second photodetector to measure the auxiliary measurement intensity.

17. The system of claim 16, wherein the first photodetector is configured to acquire light that passes through the culture solution and the culture container, and wherein the second photodetector is configured to acquire light that passes through the culture container without passing through the culture solution.

18. The system of claim 16, wherein the first position is lower than the placement surface, wherein the second position is higher than the placement surface, and wherein the control apparatus is configured to control the second photodetector to detect light reflected by a liquid surface of the culture solution or light reflected by a top plate of the culture container.

19. The system according to claim 6, wherein, to measure the baseline intensity, the processor is configured to control the one or more photodetectors to:
  measure, as a first baseline intensity, an intensity of light that has passed through the solution and the culture container, and has a first wavelength at which the absorbance of the pH indicator is pH-dependent; and
  measure, as a second baseline intensity, an intensity of light that has passed through the solution and the culture container and has a second wavelength at which the absorbance of the pH indicator is not pH-dependent, wherein, to measure the measurement intensity, the processor is configured to control the one or more photodetectors to:
  measure, as a first measurement intensity, an intensity of light that has the first wavelength and has passed through the culture solution and the culture container; and
  measure, as a second measurement intensity, an intensity of light that has the second wavelength and has passed through the culture solution and the culture container, wherein, to measure the auxiliary baseline intensity, the processor is configured to control the one or more photodetectors to measure, as the auxiliary baseline intensity, the intensity of the light from the light source that has the first wavelength and the intensity of the light from the light source that has the second wavelength when measuring the baseline intensity, wherein, to measure the auxiliary measurement intensity, the processor is configured to control the one or more photodetectors to measure, as the auxiliary baseline intensity, the intensity of the light from the light source that has the first wavelength and the intensity of the light from the light source that has the second wavelength when measuring the baseline intensity, and wherein, to calculate the absorbance of the pH indicator, the processor is configured to calculate the absorbance of the pH indicator at the first wavelength on the basis of the first baseline intensity, the second baseline intensity, the first measurement intensity, the second measurement intensity, the auxiliary baseline intensity and the auxiliary measurement intensity.

20. The system according to claim 19, wherein, to control the one or more photodetectors to measure the baseline intensity, the processor is configured to control the one or more photodetectors to measure, as a third baseline intensity, an intensity of light that has passed through the solution and the culture container, and has a third wavelength at which the absorbance of the pH indicator is pH-dependent, the third wavelength being different from the first wavelength, wherein, to control the one or more photodetectors to measure the measurement intensity, the processor is configured to control the one or more photodetectors to measure, as a third measurement intensity, an intensity of the light from the light source that has the third wavelength and has passed through the culture solution and the culture container, wherein, to control the one or more photodetectors to measure the auxiliary baseline intensity, the processor is configured to control the one or more photodetectors to measure, as the auxiliary baseline intensity, an intensity of the light from the light source that has the third wavelength and an intensity of the light from the light source that has the second wavelength when measuring the baseline intensity, wherein, to control the one or more photodetectors to measure the auxiliary measurement intensity, the processor is configured to control the one or more photodetectors to measure, as the auxiliary measurement intensity, the intensity of the light from the light source that has the third wavelength and the intensity of the light from the light source that has the second wavelength when measuring the measurement intensity, wherein the processor is further configured to calculate an absorbance of the pH indicator at the third wavelength on the basis of the third baseline intensity, the second baseline intensity, the third measurement intensity, the second measurement intensity, the auxiliary baseline intensity and the auxiliary measurement intensity, wherein, to calculate the absorbance of the pH indicator, the processor is configured to calculate the absorbance of the pH indicator at the third wavelength on the basis of the third baseline intensity, the second baseline intensity, the third measurement intensity, the second measurement intensity, the third information, and the fourth information, and wherein the processor is configured to calculate a pH of the culture solution on the basis of the absorbance of the pH indicator at the first wavelength and the absorbance of the pH indicator at the third wavelength.

21. A non-transitory computer-readable medium having stored therein a program for causing a computer to perform a process comprising:
  controlling one or more photodetectors to:
    measure, as a baseline intensity, an intensity of light that is a portion of emitted light from a light source and has passed through a solution not containing a pH indicator and a culture container;
    measure, as an auxiliary baseline intensity, an intensity of light that is a portion of emitted light from the light source and does not pass through the solution;
    after measuring the baseline intensity and the auxiliary baseline intensity, measure, as a measurement intensity, an intensity of light that is a portion of emitted light from the light source and has passed through a culture solution containing the pH indicator and the culture container; and after measuring the baseline intensity and the auxiliary baseline intensity, measure, as an auxiliary measurement intensity, an intensity of light that is a portion of emitted light from the light source and does not pass through the culture solution; and on the basis of the baseline intensity, the auxiliary baseline intensity, the measurement intensity, and the auxiliary measurement intensity, calculating an absorbance of the pH indicator at at least one wavelength included in emitted light from the light source.

* * * * *